United States Patent
Hölscher et al.

(10) Patent No.: US 11,352,587 B2
(45) Date of Patent: Jun. 7, 2022

(54) FRAGRANCE MIXTURES

(71) Applicant: Symrise AG, Holzminden (DE)

(72) Inventors: Bernd Hölscher, Halle (DE); Marc Mansfeld, Brevörde (DE); Annabel Chmelnyk, Holzminden (DE); Sven Siegel, Höxter (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 15/756,385

(22) PCT Filed: Sep. 8, 2015

(86) PCT No.: PCT/EP2015/070517
§ 371 (c)(1),
(2) Date: Feb. 28, 2018

(87) PCT Pub. No.: WO2017/041834
PCT Pub. Date: Mar. 16, 2017

(65) Prior Publication Data
US 2018/0251705 A1    Sep. 6, 2018

(51) Int. Cl.
*C11B 9/00*    (2006.01)
*C07C 67/08*    (2006.01)

(52) U.S. Cl.
CPC .......... *C11B 9/0034* (2013.01); *C07C 67/08* (2013.01); *C11B 9/0073* (2013.01); *C07C 2601/14* (2017.05); *C07C 2601/16* (2017.05)

(58) Field of Classification Search
CPC ..................................................... C11B 9/0034
See application file for complete search history.

(56) References Cited

U.S. PATENT DOCUMENTS

| | | | |
|---|---|---|---|
| 2,803,647 A | 8/1957 | Bain et al. | |
| 2016/0089464 A1* | 3/2016 | Frankenbach | A61K 8/31 424/76.1 |
| 2017/0035079 A1* | 2/2017 | Kolomeyer | A61K 8/35 |

OTHER PUBLICATIONS

Zhao et al., "Variation of essential oil of *Mentha haplocalyx* Briq. and *Mentha spicata* L. from China," Industrial Crops and Products 42 (2013), pp. 251-260.
Monforte et al., "Chemical Composition and Biological Activities of Calamintha officinalis Moench Essential Oil," Journal of Medicinal Food; 14(3) 2011), pp. 297-303.

* cited by examiner

*Primary Examiner* — Arrie L Reuther
(74) *Attorney, Agent, or Firm* — Dilworth & Barrese, LLP

(57) ABSTRACT

Suggested is a fragrance mixture comprising specific esters of (−)-carveol and/or (−)-dihydro-carveol.

10 Claims, No Drawings

FRAGRANCE MIXTURES

FIELD OF INVENTION

The present invention belongs to the area of scents and refers to new fragrance mixtures, their preparation and use in perfume and end-consumer compositions.

STATE OF THE ART

Perfume industry constantly requires new scent creations. Creating a new fragrance or perfume is associated with quite a number of challenges. For example, it is necessary to pick a specific composition of few scents out of a nearly unlimited number of possible structures know from the state of the art to satisfy a concrete need of the market and to provide a product that matches with the specific profile needed by the customer. Often, suitable scents show very advantageous performance however in combination with unpleasant and thus disadvantageous olfactory aspects, making it difficult or even impossible to use them for the specific purpose.

A second important problem refers to the need for providing scent compositions which not only match with a specific olfactory profile, but also provides so-called secondary advantageous properties. As a matter of fact, many fragrance compositions known from the market exhibit significant disadvantages in application, for example poor solubility and stability over storage, but also failures with regard to subjective issues like plentifulness, charisma and the like. In addition, a lot of known fragrance compositions require high dosages to achieve the desired olfactory result. Another prerequisite for fragrances nowadays is high biodegradability and dermatological and toxicological safety.

L-carvyl acetate (1-para-mentha-6,8-dien-2-yl acetate) has been described first in 1969 by S. Arctander (see: "Perfume and Flavour Chemicals, Vol. 1+11, Montclair, N.J., No. 582). Its trans-isomer is regarded as a natural component of spearmint oil. It provides a fresh, green-mint scent with a slight metallic aspect. The same paper makes reference to l-carvyl propionate (l-para-mentha-6,8-dien-2-yl propionate, No. 583) its scent being described as sweet, warm, mint, herbaceous with a smooth sub-note. No. 929 exhibits the scent of dihydrocarvyl acetate (para-menth-8-(9)-en-2yl-acetate; 6-menthyl-3-iso-propenyl-cyclohexanyl-acetate) as being sweet, slightly mint, bloomy, and rose-like with an herbaceous sub-note.

Zhao et al. describe variations of essential menthe oils from China containing carveol and carveol derivatives, but with no disclosure concerning the specific isomers (Industrial Crops and products, Vol. 42, p. 251-260 (2013). A similar paper concerning the composition of *Calamintha* was published by Monforte et al. The document however is also silent with regard to specific carveol isomers (J. Medicinal Food, Vol. 14(3), p. 297-303 (2011).

The object underlying the present invention has been providing a new fragrance mixture with the capability to improve positive and advantageous olfactory aspects of a fragrance and/or (simultaneously) decreasing, inhibiting and/or masking unwanted unpleasant olfactory aspects and sub-notes of fragrances. More particularly, the new fragrance mixtures should be characterised by improving stability, solubility and overall performance of fragrances as well as reducing the required dosage. Finally, the mixtures itself should exhibit excellent biodegradability and should be safe to humans and environment.

DESCRIPTION OF THE INVENTION

A first object of the present invention is a fragrance mixture comprising
(a) at least one compound of general formula (I)

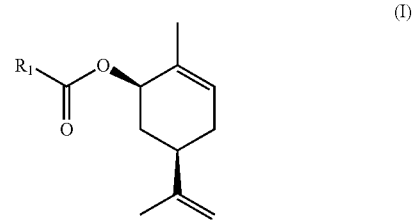

in which $R_1$ stands for methyl, ethyl, methoxy or ethoxy;
(b) at least one compound of general formula (II)

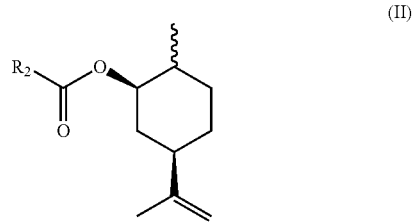

in which $R_2$ stands for methyl, ethyl, methoxy or ethoxy;
(c) at least one additional fragrance, different from compounds (I) and (II); and
(d) optionally at least one solvent.

Preferably the mixture comprises as component (b) a compound of general formula (IIa)

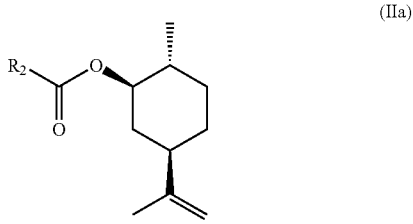

in which $R_2$ stands for methyl, ethyl, methoxy or ethoxy.

Surprisingly, it has been observed that mixtures according to the present invention are capable of supporting, increasing and/or improving olfactory properties of other fragrances, while simultaneously reducing, inhibiting and/or completely masking negative, unpleasant sub-notes of these scents. This is opposite to what a skilled person would have expected, since the compositions themselves do not exhibit a pleasant scent at all; the opposite is the case. For example, mixtures of [(1S,5S)-5-isopropenyl-2-methyl-cyclohexyl] acetate and [1S,5S)-5-isopropenyl-2-methyl-cyclohex-2-en-1-yl] acetate exhibit a scent that can be described as being metallic, oily, technical, sulphurous, garlic-like and carbide-like. However, when combined with other top-note fragrances these unpleasant notes are no longer recognized, in contrast, unpleasant sub-notes of said top note fragrances are reduced or even completely masked. The compounds according formulae (I) and (II) are completely biodegradable, safe to human and environment, easy to dissolve, storage-stable and improve impact and over-all performance and reduce dosage when blended with other fragrances.

Additional Fragrances

The additional fragrances forming group (c) are preferably chosen from the group consisting of terpenes, aldehydes, nitriles, esters, lactones and mixtures thereof. More particularly, said additional fragrances show a molecular mass of about 100 to about 250 Dalton. Suitable examples encompass members from the following groups:

Aldehydes

Examples for suitable fragrances showing an aldehyde structure encompass melonal, triplal, ligustral, adoxal, anisaldehyde, cymal, ethylvanillin, florhydral, floralozon, helional, heliotropin, hydroxycitronellal, koavon, laurinaldehyde, canthoxal, lyral, lilial, adoxal, anisaldehyde, cumal, methyl-nonyl-acetaldehyde, citronellal, citronellyloxy-acetaldehyde, cyclamenaldehyde, bourgeonal, p-tert.-bucinal, phenylacetaldehyde, undecylenaldehyde, vanillin; 2,6,10-trimethyl-9-undecenal, 3-dodecen-l-al, α-n-Amylzimtaldehyde, 4-methoxy-benzaldehyde, benzaldehyde, 3-(4-tert-butylphenyl)-propanal,2-methyl-3-(para-methoxy-phenyl propanal), 2-methyl-4-(2,6,6-trimethyl-2(1)-cyclohexen-1-yl)butanal,3-phenyl-2-propenal, cis-/trans-3,7-dimethyl-2, 6-octadien-l-al, 3,7-dimethyl-6-octen-l-al,[(3,7-dimethyl-6-octenyl)-xy]-cetaldehyde, 4-isopropylbenzyaldehyde, 1,2,3, 4,5,6,7,8-octahydro-8,8-dimethyl-2-naphthaldehyde, 2,4-dimethyl-3-cyclohexen-1-carboxyaldehyde, 2-methyl-3-(isopropyl-phenyl)propanal, decyl aldehyde, 2,6-dimethyl-5-heptenal; 4-(tricyclo[5.2.1.0 (2,6)]-decylidene-8)-butanal; octahydro-4,7-methano-IH-indenecarboxaldehyde; 3-ethoxy-4-hydroxybenzaldehyde, para-ethyl-alpha,alpha-dimethylhydrozimtaldehyde, α-methyl-3,4-(methylenedioxy)-hydrocinnamaldehyde, 3,4-methylenedioxybenzaldehyde, α-n-hexyl-cinnamaldehyde, m-cymene-7-carboxaldehyde, α-methylphenylacetaldehyde, 7-hydroxy-3,7-dimethyl octanal, undecenal, 2,4,6-trimethyl-3-cyclohexene-l-carboxalde-hyde, 4-(3)(4-methyl-3-pentenyl)-3-cyclohexen-carboxaldehyde, 1-dodecanal, 2,4-dimethyl-cyclohexene-3-carboxaldehyde,4-(4-hydroxy-4-methylpentyl)-3-cylohexene-l-carboxal-dehyde, 7-methoxy-3,7-dimethyloctan-1-al, 2-methyl undecanal, 2-methyl decanal, 1-nonanal, 1-octanal, 2,6,10-trimethyl-5, 9-undecadienal, 2-methyl-3-(4-tertbutyl)propanal, 3-(4-ethylphenyl)-2,2-dimethylpropanal, 3-(4-methoxyphenyl)-2-methylpropanal, methylnonylacetaldehyde, 2-phenylpropan-1-al, 3-phenylprop-2-en-1-al, 3-phenyl-2-pentylprop-2-en-1-al, 3-phenyl-2-hexylprop-2-enal, 3-(4-isopropylphenyl)-2-methylpropan-1-al, 3-(4-ethylphenyl)-2,2-dimethylpropan-1-al, 3-(4-tert-butylphenyl)-2-methyl-propanal, 3-(3,4-Methylendioxy-phenyl)-2-methylpropan-1-al,3-(4-Ethylphenyl)-2,2-dimethylpropanal, 3-(3-Isopropylphenyl)-butan-1-al, 2,6-Dimethylhept-5-en-1-al, Dihydrozimtaldehyde, 1-methyl-4-(4-methyl-3-pentenyl)-3-cyclohexene-1-carboxaldehyde, 5- or 6-Methoxyhexahydro-4,7-methanoindan-1 or 2-carboxyaldehyde, 3,7-dimethyloctan-1-al, 1-undecanal, 10-undecen-1-al, 4-hydroxy-3-methoxybenzaldehyde, 1-methyl-3-(4-methylpentyl)-3-cyclohexene-carboxaldehyde, 7-hydroxy-3,7-dimethyl-octanal; trans-4-decenal, 2,6-nonadienal, p-tolylacetaldehyde; 4-methylphenylacetaldehyde, 2-methyl-4-(2,6,6-trimethyl-1-cyclohexen-1-yl)-2-butenal, o-methoxyzimtaldehyde, 3,5,6-trimethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-di methyl-3-oxa-5,9-undecadien-1-al), hexahydro-4,7-methanoindan-1-carboxaldehyde, octanal, 2-methyl octanal, alpha-methyl-4-(l-methylethyl)benzene-acetaldehyde, 6,6-dimethyl-2-norpinene-2-propionaldehyde, p-methyl phenoxy acetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]-hept-5-ene-2-carbaldehyde, 9-decenal, 3-methyl-5-phenyl-1-pentanal, methylnonyl acetaldehyde, 1-p-menthene-q-carboxaldehyde, citral or its mixtures, lilial citral, 1-decanal, n-undecanal, n-dodecanal, hlorhydral, 2,4-dimethyl-3-cyclohexen-1-carboxaldehyde 4-methoxybenzaldehyde, 3-methoxy-4-hydroxy-benzaldehyde, 3-ethoxy-4-hydroxy-benzaldehyde, 3,4-methylendioxybenzaldehyde, 3,4-dimethoxybenzaldehyde and their mixtures.

As explained above, said ketones or said aldehydes may show an aliphatic, cycloaliphatic, aromatic, ethylenically unsaturated structure or a mixture of these elements. The components may also include heteroatoms or show a polycyclic structure. Suitable substituents for all these structures are hydroxyl and/or amino groups. Further fragrances are compiled in the following document: Steffen Arctander "Published 1960 and 1969 respectively, Reprinted2000 ISBN: Aroma Chemicals Vol. 1: 0-931710-37-5, Aroma Chemicals Vol. 2: 0-931710-38-3", which is hereby incorporated by reference.

Ketones

Examples for suitable fragrances showing a ketone structure encompass buccoxime, iso jasmone, methyl beta naphthyl ketone, moschus indanone, tonalid/moschus plus, α-damascone, β-damascon, δ-damascone, Iso-damascone, damascenone, damarose, methyl-dihydrojasmonate, menthone, carvone, campher, fenchone, alphalonen, β-iononw, dihydro-β-lonone, γ-methylionone, fleuramone, dihydrojasmone, cis-Jasmon, iso-E-Super, methyl cedrenylk etone, or methyl cedrylon, acetophenone, methyl aceto phenone, p-methoxyacetophenone, methyl-β-naphtyl ketone, benzylacetone, benzophenone, p-hydroxy phenylbutanone, celery Ketone or livescon, 6-osopropyl-deca-hydro-2-naphtone, dimethyloctenone, freskomenth, 4-(l-ethoxyvinyl)-3,3,5,5,-tetramethylv cyclohexanone, methylheptenone, 2-(2-(4-Methyl-3-cyclohexen-1-yl)propyl)-cyclopentanone, 1-(p-menthene-6(2)-yl)-1-propanone,4-(4-Hydroxy-3-methoxyphenyl)-2-butanone, 2-Acetyl-3,3-dimethyl-norbornan, 6,7-dihydro-1,1,2,3,3-pentamethyl-4(5H)-indanone, 4-damascol, dulcinyl or cassione, gelsone, hexalone, isocyclemone E, Methylcyclocitrone, methyl lavender ketone, orivone, p-tert-butyl cyclohexanone, verdone, delphone, muscone, neobutenone, plicatone, veloutone, 2,4, 4,7-tetramethyl-oct-6-en-3-one, tetrameran, hedion and their mixtures. The preferred ketones are selected from the group comprising α-damascone, δ-damascone, iso-damascone, carvone, γ-methyl ionone, Iso-E-Super, 2,4,4,7-tetramethyl-oct-6-en-3-one, benzylacetone, β-damascone, damascenone, methyl dihydrojasmonate, methyl cedrylone, hedione and their mixtures Alcohols Suitable fragrance alcohols encompass for example 10-undecen-1-ol, 2,6-dimethylheptan-2-ol, 2-methylbutanol, 2-methylpentanol,2-phenoxyethanol, 2-phenylpropanol, 2-tert-Butycyclohexanol, 3,5,5-trimethylcyclohexanol, 3-hexanol, 3-methyl-5-phenylpentanol, 3-octanol, 1-octen-3-ol, 3-phenylpropanol,4-heptenol, 4-isopropylcyclohexanol, 4-tert-butycyclohexanol, 6,8-dimethyl-2-nonanol,6-nonen-1-ol, 9-decen-1-ol, α-methyl benzylalcohol, α-terpineol, amylsalicylat, benzyl alcohol, benzyl salicylate, β-terpineol, butyl salicylate, citronellol, cyclohexyl salicylate, decanol, dihydromyrcenol, dimethyl benzylcarbinol, dimethyl heptanol, dimethyl octanol, ethyl salicylate, ethyl vanilin, anethol, eugenol, geraniol, heptanol, hexyl salicylat, isoborneol, isoeugenol, isopulegol, linalool, menthol, myrtenol, n-hexanol, nerol, nonanol, octanol, para-menthan-7-ol, phenylethylalkohol, phenol, phenyl salicylat, tetrahydro geraniol, tetrahydro linalool, thymol, trans-2-cis-6-nonadienol, trans-2-nonen-1-ol, trans-2-octenol, undecanol, vanillin, cinnamalcohol and their mixtures.

Esters

Examples for suitable fragrances showing a ketone structure encompass benzyl acetate, phenoxyisobutyrate, p-tert.-butylcyclohexylacetate, linalylacetate, dimethylbenzyl-carbinylacetate (DMBCA), phenylethylacetate, benzylacetate, ethylmethylphenylglycinate, allylcyclohexylpropionate, styrallylpropionate, benzylsalicylate, cyclohexylsalicylate, floramat, melusat, jasmacyclatat and their mixtures.

Ethers

Examples for suitable fragrances showing a ketone structure encompass benzylethyl ether or ambroxan Hydrocarbons Examples for suitable fragrances representing hydrocarbons encompass terpenes, e.g. limonen and pinen.

Solvents

Suitable solvents forming component (d) are sometimes advantageous to improve compatibility of the mixtures of compounds (I) and (II) with the additional fragrances.

Preferably said solvents represent alcohols, ether s or esters, such as ethanol, isopropyl alcohol, ethylene glycol, diethylene glycol, diethylene glycol monomethyl ether, diethylene glycol monoethyl ether, propylene glycol, dipropylene glycol, 1,2-butylene glycol, glycerol, diethyl phthalate, triethyl citrate, isopropyl myristate and its mixtures.

Mixtures

The compounds according formulae (I) and (II) are individually known from the state of the art. Preferred compounds according formula (I) encompass for example:

[(1R,5R)-5-Isopropenyl-2-methyl-cyclohex-2-en-1-yl] acetate,
[(1R,5R)-5-Isopropenyl-2-methyl-cyclohex-2-en-1-yl] propionate,
[(1R,5R)-5-Isopropenyl-2-methyl-cyclohex-2-en-1-yl] methyl carbonate,
[(1R,5R)-5-Isopropenyl-2-methyl-cyclohex-2-en-1-yl] ethyl carbonate.

Preferred compounds of formula (II) comprise for example:

[(1S,5R)-5-Isopropenyl-2-methyl-cyclohexyl] acetate,
[(1S,5R)-5-Isopropenyl-2-methyl-cyclohexyl] propionate,
[(1S,5R)-5-Isopropenyl-2-methyl-cyclohexyl] methylcarbonate,
[(1S,5R)-5-Isopropenyl-2-methyl-cyclohexyl] ethylcarbonate, As indicated above, the preferred species within group (b) are described by formula (IIa). More particularly the mixtures comprise the following individuals:

[(1R,2R,5R)-5-Isopropenyl-2-methyl-cyclohexyl] acetate,
[(1R,2R,5R)-5-Isopropenyl-2-methyl-cyclohexyl] propionate,
[(1R,2R,5R)-5-Isopropenyl-2-methyl-cyclohexyl] methylcarbonate,
[(1R,2R,5R)-5-Isopropenyl-2-methyl-cyclohexyl] ethylcarbonaet, Preferably the mixture of the present invention comprise said components (a) and (b) in a ratio by weight of from about 1:99 to about 99:1, more preferably in a ratio by weight of from about 10:90 to about 90:10 and particularly in a ratio by weight of from about 51:49 to about 95:5.

In another preferred embodiment of the present invention the mixtures further comprise at least one compound of formula (III)

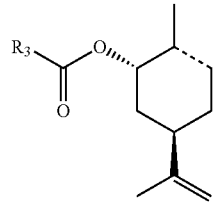

(III)

in which $R_3$ stands for methyl, ethyl, methoxy or ethoxy and the dotted line means a single or double bond.

The present invention also refers to a mixture comprising
(i) about 62 to about 67% b.w. of at least one 1R,5R isomer of compound (I);
(ii) about 14 to about 18% b.w. of at least one 1R,2R,5R isomer of compound (IIa);
(iii) about 6.0 to about 7.0% b.w. of at least one 1S,2R,5S isomer of compound (II);
(iv) about 7.0 to about 9.0% b.w. of at least one 1R,5S isomer of compound (III);
(v) about 4.0 to about 6.0% b.w. of at least one 1R,2S,5S isomer of formula (III); and
(vi) about 0.5 to about 1.0% b.w. of at least one 1R,2R,5S isomer of formula (III) on condition that the amounts add to 100% b.w.

Carveol Esters

As indicated above, individual carveol esters are known from the state of the art. For example, U.S. Pat. No. 2,803,647 (GLIDDEN CO.) discloses a process for obtaining dihydrocarvyl esters by pyrolysis of a diester of dihydrosoberol. This process requires high temperatures and a specific reactor and is therefore disadvantageous for industrial production.

Another object of the present invention is therefore related to a new process for manufacturing of any of compounds (I), (II) and/or (III) comprising the following steps:

(A) providing a source of (−)-carveol and/or (−)-dihydrocarveol;
(B) reacting said source of (−)-carveol and/or (−)-dihydrocarveol with a compound of general formula (IV)

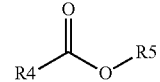

(IV)

in which $R_4$ stands for a chlorine, methyl or ethyl group and $R_5$ is selected from a methyl, ethyl, acetyl or propionyl group to form an ester.

Preferably, compound (IV) is selected from with methyl chloroformate, ethyl chloroformate, acetic anhydride or propionic anhydride A preferred embodiment of the present invention refers to a process wherein a mixture of (−)-carveol and (−)-dihydrocarveol is reacted with methyl chloroformate, ethyl chloroformate, acetic anhydride or propionic anhydride to form an ester, said (−)-carveol and (−)-dihydrocarveol being present in a ratio by weight of from about 1:99 to about 99:1, preferably about 10:90 to about 90:10 and particularly about 51:49 to about 95:5 wherein the pH-value during the esterification is maintained between about 6 and about 9.

Perfume Compositions

Another object of the present invention is related to a perfume composition comprising or consisting of the fragrance mixture encompassing components (a), (b), (c) and optionally (d) as described above. Preferably, said composition may comprise about 0.001 to about 75% b.w., more preferably about 0.01 to about 50% b.w. and particularly about 0.1 to about 5% b.w. of the mixture of compounds (I) and (II). The perfume compositions may be applied directly to skin or for example as raw material for perfume oils, perfume extracts, eau de toilettes, after shaves, eau de colognes, pre-shave products, splash colognes and air refresher. Its major advantage can be seen it their high compatibility with various additives.

Cosmetic Compositions

Another object of the present invention refers to cosmetic or personal care compositions either comprising the mixture of components (a), (b), (c) and optionally (d) as described above or the perfume compositions comprising them. The cosmetic or personal care composition may represent a skin care, hair care and/or sun care product, such as for example a cosmetic cream, lotion, spray, emulsion, ointment, gel or mouse and the like. Typical examples are skin creams and hair shampoos, antiperspirants and soaps.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, ant-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactants

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineraloladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$- fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:

products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;

$C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Belling®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphoteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and microwaxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consistiung of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivativesand indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
  p-aminobenzoic acid
  p-aminobenzoic acid ethyl ester (25 mol) ethoxylated (INCI name: PEG-25 PABA)
  p-dimethylaminobenzoic acid-2-ethylhexyl ester
  p-aminobenzoic acid ethyl ester (2 mol) N-propoxylated
  p-aminobenzoic acid glycerol ester
  salicylic acid homomenthyl ester (homosalates) (Neo Heliopan®HMS)
  salicylic acid-2-ethylhexyl ester (Neo Heliopan®OS)
  triethanolamine salicylate
  4-isopropyl benzyl salicylate
  anthranilic acid menthyl ester (Neo Heliopan®MA)
  diisopropyl cinnamic acid ethyl ester
  p-methoxycinnamic acid-2-ethylhexyl ester (Neo Heliopan®AV)
  diisopropyl cinnamic acid methyl ester
  p-methoxycinnamic acid isoamyl ester (Neo Heliopan®E 1000)
  p-methoxycinnamic acid diethanolamine salt
  p-methoxycinnamic acid isopropyl ester
  2-phenylbenzimidazole sulfonic acid and salts (Neo Heliopan®Hydro)
  3-(4'-trimethylammonium) benzylidene bornan-2-one methyl sulfate
  beta-imidazole-4(5)-acrylic acid (urocanic acid)
  3-(4'-sulfo)benzylidene bornan-2-one and salts
  3-(4'-methyl benzylidene)-D,L-camphor (Neo Heliopan®MBC)
  3-benzylidene-D,L-camphor
  N-[(2 and 4)-[2-(oxoborn-3-ylidene) methyl]benzyl] acrylamide polymer
  4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb®HEB)
  benzylidene malonate polysiloxane (Parsol®SLX)
  glyceryl ethylhexanoate dimethoxycinnamate
  dipropylene glycol salicylate
  tris(2-ethylhexyl)-4,4',4"-(1,3,5-triazine-2,4,6-triyl-triimino)tribenzoate (=2,4,6-trianilino-(p-carbo-2'-ethylhexyl-1'-oxy)-1,3,5-triazine) (Uvinul® T150).

Broadband filters which are preferably combined with one or more compounds of formula (I) in a preparation according to the present invention are selected from the group consisting of
  2-ethylhexyl-2-cyano-3,3-diphenyl acrylate (Neo Heliopan®303)
  ethyl-2-cyano-3,3'-diphenyl acrylate
  2-hydroxy-4-methoxybenzophenone (Neo Heliopan®BB)
  2-hydroxy-4-methoxybenzophenone-5-sulfonic acid
  dihydroxy-4-methoxybenzophenone
  2,4-dihydroxybenzophenone
  tetrahydroxybenzophenone
  2,2'-dihydroxy-4,4'-dimethoxybenzophenone
  2-hydroxy-4-n-octoxybenzophenone
  2-hydroxy-4-methoxy-4'-methyl benzophenone
  sodium hydroxymethoxybenzophenone sulfonate
  disodium-2,2'-dihydroxy-4,4'-dimethoxy-5,5'-disulfobenzophenone
  phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)
  2,2'-methylene bis-(6-(2H-benzotriazol-2-yl)-4-1,1,3,3-tetramethylbutyl) phenol) (Tinosorb® M)
  2,4-bis-[4-(2-ethylhexyloxy)-2-hydroxyphenyl]-1,3,5-triazine
  2,4-bis-[{(4-(2-ethylhexyloxy)-2-hydroxy}phenyl]-6-(4-methoxyphenyl)-1,3,5-triazine (Tinosorb® S)
  2,4-bis-[{(4-(3-sulfonato)-2-hydroxypropyloxy)-2-hydroxy}phenyl]-6-(4-methoxyphenyl)-1,3,5-triazine sodium salt
  2,4-bis-[{(3-(2-propyloxy)-2-hydroxypropyloxy)-2-hydroxy}phenyl]-6-(4-methoxyphenyl)-1,3,5-triazine
  2,4-bis-[{4-(2-ethylhexyloxy)-2-hydroxy}phenyl]-6-[4-(2-methoxyethyl carbonyl) phenylamino]-1,3,5-triazine
  2,4-bis-[{4-(3-(2-propyloxy)-2-hydroxypropyloxy)-2-hydroxy}phenyl]-6-[4-(2-ethylcarboxyl) phenylamino]-1,3,5-triazine
  2,4-bis-[{4-(2-ethylhexyloxy)-2-hydroxy}phenyl]-6-(1-methylpyrrol-2-yl)-1,3,5-triazine
  2,4-bis-[{4-tris-(trimethylsiloxysilylpropyloxy)-2-hydroxy}phenyl]-6-(4-methoxyphenyl)-1,3,5-triazine
  2,4-bis-[{4-(2"-methylpropenyloxy)-2-hydroxy}phenyl]-6-(4-methoxyphenyl)-1,3,5-triazine
  2,4-bis-[{4-(1',1',1',3',5',5',5'-heptamethylsiloxy-2"-methylpropyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of 4-isopropyl dibenzoyl methane terephthalylidene dibornane sulfonic acid and salts (Mexoryl®SX)

4-t-butyl-4'-methoxydibenzoyl methane (avobenzone)/ (Neo Heliopan®357)

phenylene bis-benzimidazyl tetrasulfonic acid disodium salt (Neo Heliopan®AP)

2,2'-(1,4-phenylene)-bis-(1H-benzimidazole-4,6-disulfonic acid), monosodium salt 2-(4-diethylamino-2-hydroxybenzoyl) benzoic acid hexyl ester (Uvinul A Plus)

indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of p-aminobenzoic acid 3-(4'-trimethylammonium) benzylidene bornan-2-one methyl sulfate salicylic acid homomenthyl ester (Neo Heliopan®HMS)

2-hydroxy-4-methoxybenzophenone (Neo Heliopan®BB)

2-phenylbenzimidazole sulfonic acid (Neo Heliopan®Hydro)

terephthalylidene dibornane sulfonic acid and salts (Mexoryl®SX)

4-tert-butyl-4'-methoxydibenzoyl methane (Neo Heliopan®357)

3-(4'-sulfo)benzylidene bornan-2-one and salts 2-ethylhexyl-2-cyano-3,3-diphenyl acrylate (Neo Heliopan®303)

N-[(2 and 4)-[2-(oxoborn-3-ylidene) methyl]benzyl] acrylamide polymer p-methoxycinnamic acid-2-ethylhexyl ester (Neo Heliopan®AV)

p-aminobenzoic acid ethyl ester (25 mol) ethoxylated (INCI name: PEG-25 PABA)

p-methoxycinnamic acid isoamyl ester (Neo Heliopan®E1000)

2,4,6-trianilino-(p-carbo-2'-ethylhexyl-1'-oxy)-1,3,5-triazine (Uvinul®T150)

phenol, 2-(2H-benzotriazol-2-yl)-4-methyl-6-(2-methyl-3 (1,3,3,3-tetramethyl-1-(trimethylsilyl)oxy)disiloxanyl) propyl) (Mexoryl®XL)

4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb HEB)

3-(4'-methyl benzylidene)-D,L-camphor (Neo Heliopan®MBC)

3-benzylidene camphor salicylic acid-2-ethylhexyl ester (Neo Heliopan®OS)

4-dimethylaminobenzoic acid-2-ethylhexyl ester (Padimate O)

hydroxy-4-methoxybenzophenone-5-sulfonic acid and Na salt 2,2'-methylene bis-(6-(2H-benzotriazol-2-yl)-4-1,1,3,3-tetramethylbutyl) phenol) (Tinosorb®M)

phenylene bis-benzimidazyl tetrasulfonic acid disodium salt (Neo Heliopan®AP)

2,4-bis-[{(4-(2-ethylhexyloxy)-2-hydroxy}phenyl]-6-(4-methoxyphenyl)-1,3,5-triazine (Tinosorb®S)

benzylidene malonate polysiloxane (Parsol®SLX)

menthyl anthranilate (Neo Heliopan®MA)

2-(4-diethylamino-2-hydroxybenzoyl) benzoic acid hexyl ester (Uvinul® A Plus)

indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin and/or Hair Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacin-amide), zinc salts, preferably zinc chloride or zinc gluconate, thujaplicin and derivatives, triterpenes, preferably maslinic acid, sterols, preferably ergosterol, benzofuranones, preferably senkyunolide, vinyl guaicol, ethyl guaicol, dionic acids, preferably octadecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of rumex and ramulus species, extracts of pine species (pinus), extracts of vitis species or stilbene derivatives isolated or concentrated therefrom, saxifrage extract, scutelleria extract, grape extract and/or microalgae extract, in particular Tetraselmis suecica Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular Isochrysis galbana, trehalose, erythru-lose and dihydroxyacetone. Flavonoids which bring about skin and hair tinting or brown-ing (e.g. quercetin, rhamnetin, kaempferol, fisetin, genistein, daidzein, chrysin and api-genin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulators, anti-inflammatory agents, TRPV1 antagonists and plant extracts.

Antioxidants. Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, *Phyllanthus emblica* or St. John's wort, grape seeds, wheat germ, *Phyllanthus emblica,* coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to aout 10% b.w. based on the total weight of the formulation.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, Rubus Fruticosus (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-moisturizing agents. Preferred skin moisturizing agents are selected from the group consisting of alkane diols or alkane triols comprising 3 to 12 carbon atoms, preferably $C_3$-$C_{10}$-alkane diols and $C_3$-$C_{10}$-alkane triols. More preferably the skin moisturizing agents are selected from the group consisting of: glycerol, 1,2-propylene glycol, 1,2-butylene glycol, 1,3-butylene glycol, 1,2-pentanediol, 1,2-hexanediol, 1,2-octanediol and 1,2-decanediol.

Glycosaminoglycan stimulators. Preferred compositions comprise substances stimulating the synthesis of glycosaminoglycans selected from the group consisting of hyaluronic acid and derivatives or salts, Subliskin (Sederma, INCI: Sinorhizobium Meliloti Ferment Filtrate, Cetyl Hydroxyethylcellulose, Lecithin), Hyalufix (BASF, INCI: Water, Butylene Glycol, *Alpinia galanga* leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, *Arctium lappa* fruit extract, *Eriobotrya japonica* extract, Genkwanin, N-Methyl-L-serine, (−)-alpha-bisabolol or synthetic alpha-bisabolol such as e.g. Dragosantol and Dragosantol 100 from Symrise, oat glucan, *Echinacea purpurea* extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, *Echinacea purpurea* extract, Sinorhizobium Meliloti Ferment Filtrate, Calcium ketogluconate, *Alpinia galanga* leaf extract and tetradecyl aminobutyroylvalylaminobutyric urea trifluoroacetate.

Anti-inflammatory agents. The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, Commiphora species, Rubia species, willow, willow-herb, oats, calendula, arnica, St John's wort, honeysuckle, rosemary, Passiflora incarnata, witch hazel, ginger or Echinacea; preferably selected from the group consisting of extracts or fractions from camomile, Aloe vera, oats, calendula, arnica, honeysuckle, rosemary, witch hazel, ginger or Echinacea, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenan-thramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and β-glucans, in particular 1,3-1,4-β-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of Vanillosmopsis (in particular Vanillosmopsis erythropappa or Vanillosmopsis arborea). Synthetic alpha-bisabolol is obtainable, for example, under the name "Dragosantol" from Symrise.

In case ginger extract is used in the context of the present invention, preferably extracts of the fresh or dried ginger root are used which are prepared by extraction with methanol, ethanol, iso-propanol, acetone, ethyl acetate, carbon dioxide ($CO_2$), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

TRPV1 antagonists. Suitable compounds which reduce the hypersensitivity of skin nerves based on their action as TRPV1 antagonists, encompass e.g. trans-4-tert-butyl cyclohexanol as described in WO 2009 087242 A1, or indirect modulators of TRPV1 by an activation of the μ-receptor, e.g. acetyl tetrapeptide-15, are preferred.

Desquamating agents. The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of Sophora japonica; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, a-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-cellulite agents. Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479.

Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

Fat enhancing agents. Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name:) Sym3D®).

Hair Growth Activators or Inhibitors

Formulations and products according to the present invention may also comprise one or more hair growth activators, i.e. agents to stimulate hair growth. Hair growth activators are preferably selected from the group consisting of pyrimidine derivatives such as 2,4-diaminopyrimidine-3-oxide (Aminexil), 2,4-diamino-6-piperidinopyrimidine-3-oxide (Minoxidil) and derivatives thereof, 6-amino-1,2-dihydro-1-hydroxy-2-imino-4-piperidinopyrimidine and its derivatives, xanthine alkaloids such as caffeine, theobromine and theophylline and derivatives thereof, quercetin and derivatives, dihydroquercetin (taxifolin) and derivatives, potassium channel openers, antiandrogenic agents, synthetic or natural 5-reductase inhibitors, nicotinic acid esters such as tocopheryl nicotinate, benzyl nicotinate and C1-C6 alkyl nicotinate, proteins such as for example the tripeptide Lys-Pro-Val, diphencypren, hormons, finasteride, dutasteride, flutamide, bicalutamide, pregnane derivatives, progesterone and its derivatives, cyproterone acetate, spironolactone and other diuretics, calcineurin inhibitors such as FK506 (Tacrolimus, Fujimycin) and its derivatives, Cyclosporin A and derivatives thereof, zinc and zinc salts, polyphenols, procyanidins, proanthocyanidins, phytosterols such as for example beta-sitosterol, biotin, eugenol, (±)-beta-citronellol, panthenol, glycogen for example from mussels, extracts from microorganisms, algae, plants and plant parts of for example the genera dandelion (*Leontodon* or *Taraxacum*), *Orthosiphon, Vitex, Coffea, Paullinia, Theobroma, Asiasarum, Cucurbita* or *Styphnolobium, Serenoa repens* (saw palmetto), *Sophora flavescens, Pygeum africanum, Panicum miliaceum, Cimicifuga racemosa, Glycine max, Eugenia caryophyllata, Cotinus coggygria, Hibiscus rosa-sinensis, Camellia sinensis, Ilex paraguariensis, Isochrysis galbana,* licorice, grape, apple, barley or hops or/nd hydrolysates from rice or wheat.

Alternatively, formulations and products according to the present invention may comprise one or more hair growth inhibitors (as described above), i.e. agents to reduce or prevent hair growth. Hair growth inhibitors are preferably selected from the group consisting of activin, activin derivatives or activin agonists, ornithine decarboxylase inhibitors such as alpha-difluoromethylornithine or pentacyclic triterpenes like for example ursolic acid, betulin, betulinic acid, oleanolic acid and derivatives thereof, 5alpha-reductase inhibitors, androgen receptor antagonists, S-adenosylmethionine decarboxylase inhibitors, gamma-glutamyl transpeptidase inhibitors, transglutaminase inhibitors, soybean-derived serine protease inhibitors, extracts from microorganisms, algae, different microalgae or plants and plant parts of for example the families Leguminosae, Solanaceae, Graminae, Asclepiadaceae or Cucurbitaceae, the genera *Chondrus, Gloiopeltis, Ceramium, Durvillea, Glycine max, Sanguisorba officinalis, Calendula officinalis, Hamamelis virginiana, Arnica montana, Salix alba, Hypericum perforatum* or *Gymnema sylvestre.*

Physiological Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (l-menthoxy)-1,2-propandiol, (1-menthoxy)-2-methyl-1,2-propandiol, 1-menthyl-methylether), menthylesters (for example menthylformiate, menthylacetate, menthylisobutyrate, menthyllactates, L-menthyl-L-lactate, L-menthyl-D-lactate, menthyl-(2-methoxy)acetate, menthyl-(2-methoxyethoxy) acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or $N^\alpha$-(menthanecarbonyl)glycinethylester [WS5], as described in U.S. Pat. No. 4,150,052, menthanecarboxylic acid-N-(4-cyanophenyl)amide or menthane-carboxylic acid-N-(4-cyanomethylphenyl)amide as described in WO 2005 049553 A1, methanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (l-(−)-isopulegol, 1-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2).

Anti-Inflammatory Agents

Suitable anti-inflammatory agents may be selected from the group formed by:
(i) steroidal anti-inflammatory substances of the corticosteroid type, in particular hydrocortisone, hydrocortisone derivatives such as hydrocortisone 17-butyrate, dexamethasone, dexamethasone phosphate, methylprednisolone or cortisone,
(ii) non-steroidal anti-inflammatory substances, in particular oxicams such as piroxicam or tenoxicam, salicylates such as aspirin, disalcid, solprin or fendosal, acetic acid derivatives such as diclofenac, fenclofenac, indomethacin, sulindac, tolmetin or clindanac, fenamates such as mefenamic, meclofenamic, flufenamic or niflumic, propionic acid derivatives such as ibuprofen, naproxen or benoxaprofen, pyrazoles such as phenylbutazone, oxyphenylbutazone, febrazone or azapropazone,
(iii) natural or naturally occuring anti-inflammatory substances or substances that alleviate reddening and/or itching, in particular extracts or fractions from camomile, *Aloe vera, Commiphora* species, *Rubia* species, willow, willow-herb, oats, calendula, arnica, St John's wort, honeysuckle, rosemary, *Passiflora incarnata,* witch hazel, ginger or *Echinacea,* or single active compounds thereof,
(iv) histamine receptor antagonists, serine protease inhibitors (e.g. of Soy extracts), TRPV1 antagonists (e.g. 4-t-Butylcyclohexanol), NK1 antagonists (e.g. Aprepitant, Hydroxyphenyl Propamidobenzoic Acid), cannabinoid receptor agonists (e.g. Palmitoyl Ethanolamine) and TRPV3 antagonists.

Physiological Cooling Agents

Suitable physiological cooling agents may be selected from the group consisting of menthol, menthone glycerol acetal, menthone glyceryl ketal, menthyl lactate preferably l-menthyl lactate, in particular l-menthyl l-lactate), menthyl ethyl oxamate, substituted menthyl-3-carboxylic acid amides (e.g. menthyl-3-carboxylic acid N-ethylamide, $N^\alpha$-(L-menthanecarbonyl)glycine ethyl ester, 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, monomenthyl glutarate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate and icilin.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen CAT). The substances inhibit enzyme activity, thereby reducing the formation of odour. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odour Absorbers and Antiperspirant Active Agents

Suitable odour absorbers are substances which are able to absorb and largely retain odour-forming compounds. They lower the partial pressure of the individual components, thus also reducing their rate of diffusion. It is important that perfumes must remain unimpaired in this process. Odour absorbers are not effective against bacteria. They comprise, for example, as main constituent, a complex zinc salt of ricinoleic acid or specific, largely odour-neutral fragrances which are known to the person skilled in the art as "fixatives", such as, for example, extracts of labdanum or styrax or certain abietic acid derivatives. The odour masking agents are fragrances or perfume oils, which, in addition to their function as odour masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal products, such as, for example, civet and castoreum. Typical synthetic fragrance compounds are products of the ester, ether, aldehyde, ketone, alcohol, and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linaool, phenylethyl alcohol and terpineol, and the hydrocarbons include mainly the terpenes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden flower oil, juniperberry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine.

Film Formers and Anti-Dandruff Agents

Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

Suitable antidandruff agents are Pirocton Olamin (1-hydroxy-4-methyl-6-(2,4,4-trimethylpentyl)-2-(1H)-pyridinone monoethanolamine salt), Baypival (Climbazole), Ketoconazol® (4-acetyl-1-{4-[2-(2,4-dichlorophenyl) r-2-(1H-imidazol-1-ylmethyl)-1,3-dioxylan-c-4-ylmethoxyphenyl}- piperazine, ketoconazole, elubiol, selenium disulfide, colloidal sulfur, sulfur polyethylene glycol sorbitan monooleate, sulfur ricinol polyethoxylate, sulfur tar distillate, salicylic acid (or in combination with hexachlorophene), undecylenic acid, monoethanolamide sulfosuccinate Na salt, Lamepon® UD (protein/undecylenic acid condensate), zinc pyrithione, aluminium pyrithione and magnesium pyrithione/dipyrithione magnesium sulfate.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;
alkylene glycols such as, for example, ethylene glycol, diethylene glycol, propylene glycol, butylene glycol, hexylene glycol and polyethylene glycols with an average molecular weight of 100 to 1000 Dalton;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol,
sugars containing 5 to 12 carbon atoms, for example glucose or sucrose;
amino sugars, for example glucamine;
dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, ■--isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO (OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, anti-dandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Household Compositions

Another object of the present invention refers to household or detergent compositions either comprising the mixture of components (a), (b), (c) and optionally (d) as described above or the perfume compositions comprising them. Suitable examples for household and detergent products encompass heavy duty powder detergents, heavy duty liquid detergents, light duty powder detergents, light duty liquid detergents, fabric softeners, manual dish wash agents, all-purpose cleaners and the like.

The detergent compositions according to the present invention may comprise any of the ingredients customarily found in such compositions, such as, for example, anionic, nonionic, cationic, amphoteric or zwitterionic (co-)surfactants, organic solvents, builders, enzymes and additional auxiliaries such as soil repellents, thickeners, colorants and fragrances or the like.

Anionic Co-Surfactants

Preferably, surfactants of the sulfonate type, alk(en)yl sulfonates, alkoxylated alk(en)yl sulfates, ester sulfonates and/or soaps are used as the anionic surfactants. Suitable surfactants of the sulfonate type are advantageously $C_{9-13}$ alkylbenzene sulfonates, olefin sulfonates, i.e. mixtures of alkene- and hydroxyalkane sulfonates, and disulfonates, as are obtained, for example, by the sulfonation with gaseous sulfur trioxide of $C_{12-18}$ monoolefins having a terminal or internal double bond and subsequent alkaline or acidic hydrolysis of the sulfonation products.

Alk(en)yl sulfates. Preferred alk(en)yl sulfates are the alkali and especially the sodium salts of the sulfuric acid half-esters of the $C_{12}$-$C_{18}$ fatty alcohols, for example, from coconut butter alcohol, tallow alcohol, lauryl, myristyl, cetyl or stearyl alcohol or from $C_8$-$C_{20}$ oxo alcohols and those half-esters of secondary alcohols of these chain lengths. Alk(en)yl sulfates of the cited chain lengths that comprise a synthetic straight chain alkyl group manufactured petro-chemically are also preferred. The $C_{12}$-$C_{16}$ alkyl sulfates and $C_{12}$-$C_{15}$ alkyl sulfates as well as $C_{14}$-$C_{15}$ alkyl sulfates and $C_{14}$-$C_{16}$ alkyl sulfates are particularly preferred on the grounds of laundry performance. The 2,3-alkyl sulfates, which can be obtained from Shell Oil Company under the trade name DAN™, are also suitable anionic surfactants.

Alk(en)yl ether sulfates. Sulfuric acid mono-esters derived from straight-chained or branched $C_7$-$C_{21}$ alcohols ethoxylated with 1 to 6 moles ethylene oxide are also suitable, such as 2-methyl-branched $C_9$-$C_{11}$ alcohols with an average of 3.5 mol ethylene oxide (EO) or $C_{12}$-$C_{18}$ fatty alcohols with 1 to 4 EO.

Ester sulfonates. The esters of alpha-sulfo fatty acids (ester sulfonates), e.g., the alpha-sulfonated methyl esters of hydrogenated coco-, palm nut- or tallow acids are likewise suitable.

Soaps. Soaps, in particular, can be considered as further anionic surfactants. Saturated fatty acid soaps are particularly suitable, such as the salts of lauric acid, myristic acid, palmitic acid, stearic acid, hydrogenated erucic acid and behenic acid, and especially soap mixtures derived from natural fatty acids such as coconut oil fatty acid, palm kernel oil fatty acid or tallow fatty acid. Those soap mixtures are particularly preferred that are composed of 50 to 100 wt. % of saturated $C_{12}$-$C_{24}$ fatty acid soaps and 0 to 50 wt. % of oleic acid soap.

Ether carboxylic acids. A further class of anionic surfactants is that of the ether carboxylic acids, obtainable by treating fatty alcohol ethoxylates with sodium chloroacetate in the presence of basic catalysts. They have the general formula: $RO(CH_2CH_2O)_pCH_2COOH$ with R=$C_1$-$C_{18}$ and p=0.1 to 20. Ether carboxylic acids are insensitive to water hardness and possess excellent surfactant properties.

Non-Ionic (Co-)Surfactants

Alcohol alkoxylates. The added nonionic surfactants are preferably alkoxylated and/or propoxylated, particularly primary alcohols having preferably 8 to 18 carbon atoms and an average of 1 to 12 mol ethylene oxide (EO) and/or 1 to 10 mol propylene oxide (PO) per mol alcohol. $C_8$-$C_{16}$-Alcohol alkoxylates, advantageously ethoxylated and/or propoxylated $C_{10}$-$C_{15}$-alcohol alkoxylates, particularly $C_{12}$-$C_{14}$ alcohol alkoxylates, with an ethoxylation degree between 2 and 10, preferably between 3 and 8, and/or a propoxylation degree between 1 and 6, preferably between 1.5 and 5, are particularly preferred. The cited degrees of ethoxylation and propoxylation constitute statistical average values that can be a whole or a fractional number for a specific product. Preferred alcohol ethoxylates and propoxylates have a narrowed homolog distribution (narrow range ethoxylates/propoxylates, NRE/NRP). In addition to these nonionic surfactants, fatty alcohols with more than 12 EO can also be used. Examples of these are (tallow) fatty alcohols with 14 EO, 16 EO, 20 EO, 25 EO, 30 EO or 40 EO.

Alkylglycosides (APO. Furthermore, as additional nonionic surfactants, alkyl glycosides that satisfy the general Formula RO(G)$_x$, can be added, e.g., as compounds, particularly with anionic surfactants, in which R means a primary linear or methyl-branched, particularly 2-methyl-branched, aliphatic group containing 8 to 22, preferably 12 to 18 carbon atoms and G stands for a glycose unit containing 5 or 6 carbon atoms, preferably for glucose. The degree of oligomerization x, which defines the distribution of monoglycosides and oligoglycosides, is any number between 1 and 10, preferably between 1.1 and 1.4.

Fatty acid ester alkoxylates. Another class of preferred nonionic surfactants, which are used either as the sole nonionic surfactant or in combination with other nonionic surfactants, in particular, together with alkoxylated fatty alcohols and/or alkyl glycosides, are alkoxylated, preferably ethoxylated or ethoxylated and propoxylated fatty acid alkyl esters preferably containing 1 to 4 carbon atoms in the alkyl chain, more particularly the fatty acid methyl esters which are described, for example, in Japanese Patent Application JP-A-58/217598 or which are preferably produced by the process described in International Patent Application WO-A-90/13533. Methyl esters of $C_{12}$-$C_{18}$ fatty acids containing an average of 3 to 15 EO, particularly containing an average of 5 to 12 EO, are particularly preferred.

Amine oxides. Nonionic surfactants of the amine oxide type, for example, N-coco alkyl-N,N-dimethylamine oxide and N-tallow alkyl-N,N-dihydroxyethylamine oxide, and the fatty acid alkanolamides may also be suitable. The quantity in which these nonionic surfactants are used is preferably no more than the quantity in which the ethoxylated fatty alcohols are used and, particularly no more than half that quantity.

Gemini surfactants. The so-called gemini surfactants can be considered as further surfactants. Generally speaking, such compounds are understood to mean compounds that have two hydrophilic groups and two hydrophobic groups per molecule. As a rule, these groups are separated from one another by a "spacer". The spacer is usually a hydrocarbon chain that is intended to be long enough such that the hydrophilic groups are a sufficient distance apart to be able to act independently of one another. These types of surfactants are generally characterized by an unusually low critical micelle concentration and the ability to strongly reduce the surface tension of water. In exceptional cases, however, not only dimeric but also trimeric surfactants are meant by the term gemini surfactants. Suitable gemini surfactants are, for example, sulfated hydroxy mixed ethers according to German Patent Application DE 4321022 A1 or dimer alcohol bis- and trimer alcohol tris sulfates and ether sulfates according to International Patent Application WO 96/23768 A1. Blocked end group dimeric and trimeric mixed ethers according to German Patent Application DE 19513391 A1 are especially characterized by their bifunctionality and multifunctionality. Gemini polyhydroxyfatty acid amides or polyhydroxyfatty acid amides, such as those described in International Patent Applications WO 95/19953 A1, WO 95/19954 A1 and WO 95/19955 A1 can also be used.

Cationic Co-Surfactants

Tetraalkyl ammonium salts. Cationically active surfactants comprise the hydrophobic high molecular group required for the surface activity in the cation by dissociation in aqueous solution. A group of important representatives of the cationic surfactants are the tetraalkyl ammonium salts of the general formula: $(R^1R^2R^3R^4N^+)$ $X^-$. Here R1 stands for $C_1$-$C_8$ alk(en)yl, $R^2$, $R^3$ and $R^4$, independently of each other, for alk(en)yl radicals having 1 to 22 carbon atoms. X is a counter ion, preferably selected from the group of the halides, alkyl sulfates and alkyl carbonates. Cationic surfactants, in which the nitrogen group is substituted with two long acyl groups and two short alk(en)yl groups, are particularly preferred.

Esterquats. A further class of cationic surfactants particularly useful as co-surfactants for the present invention is represented by the so-called esterquats. Esterquats are generally understood to be quaternised fatty acid triethanolamine ester salts. These are known compounds which can be obtained by the relevant methods of preparative organic chemistry. Reference is made in this connection to International patent application WO 91/01295 A1, according to which triethanolamine is partly esterified with fatty acids in the presence of hypophosphorous acid, air is passed through the reaction mixture and the whole is then quaternised with dimethyl sulphate or ethylene oxide. In addition, German patent DE 4308794 C1 describes a process for the production of solid esterquats in which the quaternisation of triethanolamine esters is carried out in the presence of suitable dispersants, preferably fatty alcohols.

Typical examples of esterquats suitable for use in accordance with the invention are products of which the acyl component derives from monocarboxylic acids corresponding to formula RCOOH in which RCO is an acyl group containing 6 to 10 carbon atoms, and the amine component is triethanolamine (TEA). Examples of such monocarboxylic acids are caproic acid, caprylic acid, capric acid and technical mixtures thereof such as, for example, so-called head-fractionated fatty acid. Esterquats of which the acyl component derives from monocarboxylic acids containing 8 to 10 carbon atoms, are preferably used. Other esterquats are those of which the acyl component derives from dicarboxylic acids like malonic acid, succinic acid, maleic acid, fumaric acid, glutaric acid, sorbic acid, pimelic acid, azelaic acid, sebacic acid and/or dodecanedioic acid, but preferably adipic acid. Overall, esterquats of which the acyl component derives from mixtures of monocarboxylic acids containing 6 to 22 carbon atoms, and adipic acid are preferably used. The molar ratio of mono and dicarboxylic acids in the final esterquat may be in the range from 1:99 to 99:1 and is preferably in the range from 50:50 to 90:10 and more particularly in the range from 70:30 to 80:20. Besides the quaternised fatty acid triethanolamine ester salts, other suitable esterquats are quaternized ester salts of mono-/dicarboxylic acid mixtures with diethanolalkyamines or 1,2-dihydroxypropyl dialkylamines. The esterquats may be obtained both from fatty acids and from the corresponding triglycerides in admixture with the corresponding dicarboxylic acids. One such process, which is intended to be representative of the relevant prior art, is proposed in European patent EP 0750606 B1. To produce the quaternised esters, the mixtures of mono- and dicarboxylic acids and the triethanolamine—based on the available carboxyl functions—may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9.

Amphoteric or Zwitterionic Co-Surfactants

Betaines. Amphoteric or ampholytic surfactants possess a plurality of functional groups that can ionize in aqueous solution and thereby—depending on the conditions of the medium—lend anionic or cationic character to the compounds (see DIN 53900, July 1972). Close to the isoelectric point (around pH 4), the amphoteric surfactants form inner salts, thus becoming poorly soluble or insoluble in water. Amphoteric surfactants are subdivided into ampholytes and betaines, the latter existing as zwitterions in solution. Ampholytes are amphoteric electrolytes, i.e. compounds that possess both acidic as well as basic hydrophilic groups and therefore behave as acids or as bases depending on the conditions. Especially betaines are known surfactants which are mainly produced by carboxyalkylation, preferably carboxymethylation, of amine compounds. The starting materials are preferably condensed with halocarboxylic acids or salts thereof, more particularly sodium chloroacetate, one mole of salt being formed per mole of betaine. The addition of unsaturated carboxylic acids, such as acrylic acid for example, is also possible. Examples of suitable betaines are the carboxy alkylation products of secondary and, in particular, tertiary amines which correspond to formula $R^1R^2R^3N$—$(CH_2)_q COOX$ where $R^1$ is a an alkyl radical having 6 to 22 carbon atoms, $R^2$ is hydrogen or an alkyl group containing 1 to 4 carbon atoms, $R^3$ is an alkyl group containing 1 to 4 carbon atoms, q is a number of 1 to 6 and X is an alkali and/or alkaline earth metal or ammonium. Typical examples are the carboxymethylation products of hexylmethylamine, hexyldimethylamine, octyldimethylamine, decyldimethylamine, $C_{12/14}$-cocoalkyldimethyl-amine, myristyldimethylamine, cetyldimethylamine, stearyldimethylamine, stearylethylmethylamine, oleyldimethylamine, $C_{16/18}$-tallowalkyldimethylamine and their technical mixtures, and particularly dodecyl methylamine, dodecyl dimethylamine, dodecyl ethylmethylamine and technical mixtures thereof.

Alkylamido betaines. Other suitable betaines are the carboxyalkylation products of amidoamines corresponding to formula $R^1CO(R^3)(R^4)$—$NH$—$(CH_2)_p$—$N$—$(CH_2)_q COOX$ in which $R^1CO$ is an aliphatic acyl radical having 6 to 22 carbon atoms and 0 or 1 to 3 double bonds, $R^2$ is hydrogen or an alkyl radical having 1 to 4 carbon atoms, $R^3$ is an alkyl radical having 1 to 4 carbon atoms, p is a number from 1 to 6, q is a number from 1 to 3 and X is an alkali and/or alkaline earth metal or ammonium. Typical examples are reaction products of fatty acids having 6 to 22 carbon atoms, like for example caproic acid, caprylic acid, caprinic acid, lauric acid, myristic acid, palmitic acid, palmoleic acid, stearic acid, isostearic acid, oleic acid, elaidic acid, petroselinic acid, linolic acid linoleic acid, elaeostearic acid, arachidonic acid, gadoleic acid, behenic acid, erucic acid and their technical mixtures with N,N-dimethylaminoethylamine, N,N-dimethylaminopropylamine, N,N-diethylaminoethylamine and N,N-diethylaminopropylamine, which are condensed with sodium chloroacetate. The commercially available products include Dehyton® K and Dehyton® PK (Cognis Deutschland GmbH & Co., KG) as well as Tego®Betaine (Goldschmidt).

Imidazolines. Other suitable starting materials for the betaines to be used for the purposes of the invention are imidazolines. These substances are also known and may be obtained, for example, by cyclizing condensation of 1 or 2 moles of $C_6$-$C_{22}$ fatty acids with polyfunctional amines, such as for example aminoethyl ethanolamine (AEEA) or diethylenetriamine. The corresponding carboxyalkylation products are mixtures of different open-chain betaines. Typical examples are condensation products of the above-mentioned fatty acids with AEEA, preferably imidazolines based on lauric acid, which are subsequently betainised with sodium chloroacetate. The commercially available products include Dehyton® G (Cognis Deutschland GmbH & Co., KG)

The amount of (co-)surfactant comprised in the inventive compositions is advantageously 0.1 wt. % to 90 wt. %, particularly 10 wt. % to 80 wt. % and particularly preferably 20 wt. % to 70 wt.-%.

Organic Solvents

Liquid light or heavy duty detergents may comprise organic solvents, preferably those miscible with water. Polydiols, ethers, alcohols, ketones, amides and/or esters are preferably used as the organic solvent for this in amounts of 0 to 90 wt. %, preferably 0.1 to 70 wt. %, particularly 0.1 to 60 wt. %. Low molecular weight polar substances, such as for example, methanol, ethanol, propylene carbonate, acetone, acetonylacetone, diacetone alcohol, ethyl acetate, 2-propanol, ethylene glycol, propylene glycol, glycerin, diethylene glycol, dipropylene glycol monomethyl ether and dimethylformamide or their mixtures are preferred.

Enzymes

Cellulase Enzymes. Cellulase enzymes optionally used in the instant detergent composition are preferably incorporated, when present, at levels sufficient to provide up to about 5 mg by weight, more preferably about 0.01 mg to about 3 mg, of active enzyme per gram of the composition. Unless stated otherwise, the compositions herein preferably comprise from about 0.001% to about 5%, preferably 0.01%-1% by weight of a commercial enzyme preparation.

The cellulases suitable for the present invention include either bacterial or fungal cellulase. Preferably, they will have a pH optimum of between 5 and 9.5. Suitable cellulases are fungal cellulase produced from Humicola insolens and Humicola strain DSM1800 or a cellulase 212-producing fungus belonging to the genus Aeromonas, and cellulase extracted from the hepatopancreas of a marine mollusk (Dolabella Auricula Solander), suitable cellulases are also disclosed in GB 2,075,028 A. In addition, cellulase especially suitable for use herein are disclosed in WO 1992 013057 A1. Most preferably, the cellulases used in the instant detergent compositions are purchased commercially from NOVO Industries A/S under the product names CAREZYMEO and CELLUZYMEO.

Other Enzymes. Additional enzymes can be included in the detergent compositions herein for a wide variety of fabric laundering purposes, including removal of protein-based, carbohydrate-based, or triglyceride-based stains, for example, and for the prevention of refugee dye transfer, and for fabric restoration. The additional enzymes to be incorporated include proteases, amylases, lipases, and peroxidases, as well as mixtures thereof. Other types of enzymes can also be included. They can be of any suitable origin, such as vegetable, animal, bacterial, fungal and yeast origin. However, their choice is governed by several factors such as pH-activity and/or stability optima, thermostability, stability versus active detergents, builders as well as their potential to cause malodors during use. In this respect bacterial or fungal enzymes are preferred, such as bacterial amylases and proteases.

Enzymes are normally incorporated at levels sufficient to provide up to about 5 mg by weight, more typically about 0.01 mg to about 3 mg, of active enzyme per gram of the composition. Stated otherwise, the compositions herein will typically comprise from about 0.001% to about 5%, preferably 0.01%-1% by weight of a commercial enzyme preparation. Protease enzymes are usually present in such commercial preparations at levels sufficient to provide from 0.005 to 0.1 Anson units (AU) of activity per gram of composition.

Suitable examples of proteases are the subtilisins which are obtained from particular strains of *B. subtilis* and *B. licheniforms*. Another suitable protease is obtained from a strain of *Bacillus*, having maximum activity throughout the pH range of 8-12, developed and sold by Novo Industries A/S under the registered trade name ESPERASE®. The preparation of this enzyme and analogous enzymes is described in GB 1,243,784 of Novo. Proteolytic enzymes suitable for removing protein-based stains that are commercially available include those sold under the trade names ALCALASE® and SAVINASE® by Novo Industries A/S and MAXATASE® by International Bio-Synthetics, Inc. Other proteases include Protease A; Protease B and proteases made by Genencor International, Inc., according to U.S. Pat. No. 5,204,015 and U.S. Pat. No. 5,244,791.

Amylases include, for example, alpha-amylases like RAPIDASE®, International Bio-Synthetics, Inc. and TERMAMYL®, Novo Industries.

Suitable lipase enzymes for detergent usage include those produced by microorganisms of the *Pseudomonas* group, such as *Pseudomonas stutzeri* ATCC 19154. This lipase is available from Amano Pharmaceutical Co. Ltd., under the trade name Lipase P "Amano". Other commercial lipases include Amano-CES, lipases ex *Chromobacter viscosum*, e.g. *Chromobacter viscosum* var. *lipolyticum* NRRLB 3673, commercially available from Toyo Jozo Co., and further *Chromobacter viscosum* lipases from U.S. Biochemical Corp. and Disoynth Co., and lipases ex *Pseudomonas gladioli*. The LIPOLASE® enzyme derived from *Humicola lanuginosa* (commercially available from Novo Industries A/S) is a preferred lipase for use herein.

Peroxidase enzymes are used in combination with oxygen sources, e.g., percarbonate, perborate, persulfate, hydrogen peroxide, etc. They are used for "solution bleaching," i.e. to prevent transfer of dyes or pigments removed from substrates during wash operations to other substrates in the wash solution. Peroxidase enzymes are known in the art, and include, for example, horseradish peroxidase, ligninase, and haloperoxidase such as chloro- and bromo-peroxidase. Peroxidase-containing detergent compositions are disclosed, for example, in WO 1989 099813 A1.

Enzyme Stabilizers. The enzymes employed herein are stabilized by the presence of water-soluble sources of calcium and/or magnesium ions in the finished detergent compositions which provide such ions to the enzymes. (Calcium ions are generally somewhat more effective than magnesium ions and are preferred herein if only one type of cation is being used.) Additional stability can be provided by the presence of various other art-disclosed stabilizers, especially borate species, see U.S. Pat. No. 4,537,706, incorporated herein in its entirety. Typical detergents, especially liquids, will comprise from about 1 to about 30, preferably from about 2 to about 20, more preferably from about 5 to about 15, and most preferably from about 8 to about 12, millimoles of calcium ion per liter of finished composition. In solid detergent compositions the formulation can include a sufficient quantity of a water-soluble calcium ion source to provide such amounts in the laundry liquor. In the alternative, natural water hardness can suffice.

It is to be understood that the foregoing levels of calcium and/or magnesium ions are sufficient to provide enzyme stability. More calcium and/or magnesium ions can be added to the compositions to provide an additional measure of grease removal performance. Accordingly, as a general proposition the compositions herein will typically comprise from about 0.05% to about 2% by weight of a water-soluble source of calcium or magnesium ions, or both. The amount can vary, of course, with the amount and type of enzyme employed in the composition.

The compositions herein can also optionally, but preferably, contain various additional stabilizers, especially borate-type stabilizers. Typically, such stabilizers will be used at levels in the compositions from about 0.25% to about 10%, preferably from about 0.5% to about 5%, more preferably from about 0.75% to about 3%, by weight of boric acid or other borate compound capable of forming boric acid in the composition (calculated on the basis of boric acid). Boric acid is preferred, although other compounds such as boric oxide, borax and other alkali metal borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

Builders

Zeolites. Fine crystalline, synthetic zeolites containing bound water can be used as builders, for example, preferably zeolite A and/or P. Zeolite MAP® (commercial product of the Crosfield company), is particularly preferred as the zeolite P. However, zeolite X and mixtures of A, X, Y and/or P are also suitable. A co-crystallized sodium/potassium aluminum silicate from Zeolite A and Zeolite X, which is available as Vegobond RX. (commercial product from Condea Augusta S.p.A.), is also of particular interest. Preferably, the zeolite can be used as a spray-dried powder. For the case where the zeolite is added as a suspension, this can comprise small amounts of nonionic surfactants as stabilizers, for example, 1 to 3 wt. %, based on the zeolite, of ethoxylated $C_{12}$-$C_{18}$ fatty alcohols with 2 to 5 ethylene oxide groups, $C_{12}$-$C_{14}$ fatty alcohols with 4 to 5 ethylene oxide groups or ethoxylated isotridecanols. Suitable zeolites have an average particle size of less than 10 µm (test method: volumetric distribution Coulter counter) and preferably comprise 18 to 22 wt. %, particularly 20 to 22 wt. % of bound water. Apart from this, phosphates can also be used as builders.

Layered silicates. Suitable substitutes or partial substitutes for phosphates and zeolites are crystalline, layered sodium silicates. These types of crystalline layered silicates are described, for example, in European Patent Application EP 0164514 A1. Preferred crystalline layered silicates are those obtained for example, from the process described in International Patent Application WO 91/08171 A1.

Amorphous silicates. Preferred builders also include amorphous sodium silicates with a modulus ($Na_2O$:$SiO_2$ ratio) of 1:2 to 1:3.3, preferably 1:2 to 1:2.8 and more preferably 1:2 to 1:2.6, which dissolve with a delay and exhibit multiple wash cycle properties. The delay in dissolution compared with conventional amorphous sodium silicates can have been obtained in various ways, for example, by surface treatment, compounding, compressing/compacting or by over-drying. In the context of this invention, the term "amorphous" also means "X-ray amorphous". In other words, the silicates do not produce any of the sharp X-ray reflexions typical of crystalline substances in X-ray diffraction experiments, but at best one or more maxima of the scattered X-radiation, which have a width of several degrees of the diffraction angle. However, particularly good builder properties may even be achieved where the silicate particles produce indistinct or even sharp diffraction maxima in electron diffraction experiments. This is to be interpreted to mean that the products have microcrystalline regions between 10 and a few hundred nm in size, values of up to at most 50 nm and especially up to at most 20 nm being preferred. This type of X-ray amorphous silicates, which similarly possess a delayed dissolution in comparison with the customary water glasses, are described, for example, in German Patent Application DE 4400024 A1. Compacted/densified amorphous silicates, compounded amorphous silicates and over dried X-ray-amorphous silicates are particularly preferred.

Phosphates. Also the generally known phosphates can also be added as builders, in so far that their use should not be avoided on ecological grounds. The sodium salts of the orthophosphates, the pyrophosphates and especially the tripolyphosphates are particularly suitable. Their content is generally not more than 25 wt. %, preferably not more than 20 wt. %, each based on the finished composition. In some cases it has been shown that particularly tripolyphosphates, already in low amounts up to maximum 10 wt. %, based on the finished composition, in combination with other builders, lead to a synergistic improvement of the secondary washing power. Preferred amounts of phosphates are under 10 wt. %, particularly 0 wt. %.

Co-Builders

Polycarboxylic acids. Useful organic cobuilders are, for example, the polycarboxylic acids usable in the form of their sodium salts of polycarboxylic acids, wherein polycarboxylic acids are understood to be carboxylic acids that carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA) and its derivatives and mixtures thereof. Preferred salts are the salts of polycarboxylic acids such as citric acid, adipic acid, succinic acid, glutaric acid, tartaric acid, sugar acids and mixtures thereof.

Organic acids. Acids per se can also be used. Besides their building effect, the acids also typically have the property of an acidifying component and, hence also serve to establish a relatively low and mild pH in detergents or cleansing compositions. Citric acid, succinic acid, glutaric acid, adipic acid, gluconic acid and any mixtures thereof are particularly mentioned in this regard. Further suitable acidifiers are the known pH regulators such as sodium hydrogen carbonate and sodium hydrogen sulfate.

Polymers. Particularly suitable polymeric cobuilders are polyacrylates, which preferably have a molecular weight of 2,000 to 20,000 g/mol. By virtue of their superior solubility, preferred representatives of this group are again the short-chain polyacrylates, which have molecular weights of 2,000 to 10,000 g/mol and, more particularly, 3,000 to 5,000 g/mol. Suitable polymers can also include substances that consist partially or totally of vinyl alcohol units or its derivatives.

Further suitable copolymeric polycarboxylates are particularly those of acrylic acid with methacrylic acid and of acrylic acid or methacrylic acid with maleic acid. Copolymers of acrylic acid with maleic acid, which comprise 50 to 90 wt. % acrylic acid and 50 to 10 wt. % maleic acid, have proven to be particularly suitable. Their relative molecular weight, based on free acids, generally ranges from 2,000 to 70,000 g/mol, preferably 20,000 to 50,000 g/mol and especially 30,000 to 40,000 g/mol. The (co)polymeric polycarboxylates can be added either as an aqueous solution or preferably as powder. In order to improve the water solubility, the polymers can also comprise allylsulfonic acids as monomers, such as, for example, allyloxybenzene sulfonic acid and methallyl sulfonic acid as in the EP 0727448 B1.

Biodegradable polymers comprising more than two different monomer units are particularly preferred, examples being those comprising, as monomers, salts of acrylic acid and of maleic acid, and also vinyl alcohol or vinyl alcohol derivatives, as in DE 4300772 A1, or those comprising, as monomers, salts of acrylic acid and of 2-alkylallyl sulfonic acid, and also sugar derivatives. Further preferred copolymers are those that are described in German Patent Applications DE 4303320 A1 and DE 4417734 A1 and preferably include acrolein and acrylic acid/acrylic acid salts or acrolein and vinyl acetate as monomers.

Similarly, other preferred builders are polymeric aminodicarboxylic acids, salts or precursors thereof. Those polyaspartic acids or their salts and derivatives disclosed in German Patent Application DE 19540086 A1 as having a bleach-stabilizing action in addition to cobuilder properties are particularly preferred.

Further suitable builders are polyacetals that can be obtained by treating dialdehydes with polyol carboxylic acids that possess 5 to 7 carbon atoms and at least 3 hydroxyl groups, as described in European Patent Application EP 0280223 A1. Preferred polyacetals are obtained from dialdehydes like glyoxal, glutaraldehyde, terephthalaldehyde as well as their mixtures and from polycarboxylic acids like gluconic acid and/or glucoheptonic acid.

Carbohydrates. Further suitable organic cobuilders are dextrins, for example, oligomers or polymers of carbohydrates that can be obtained by the partial hydrolysis of starches. The hydrolysis can be carried out using typical processes, for example, acidic or enzymatic catalyzed processes. The hydrolysis products preferably have average molecular weights in the range of 400 to 500,000 g/mol. A polysaccharide with a dextrose equivalent (DE) of 0.5 to 40 and, more particularly, 2 to 30 is preferred, the DE being an accepted measure of the reducing effect of a polysaccharide in comparison with dextrose, which has a DE of 100. Both maltodextrins with a DE between 3 and 20 and dry glucose syrups with a DE between 20 and 37 and also so-called yellow dextrins and white dextrins with relatively high molecular weights of 2,000 to 30,000 g/mol may be used. A preferred dextrin is described in British Patent Application 94 19 091.

The oxidized derivatives of such dextrins concern their reaction products with oxidizing compositions that are capable of oxidizing at least one alcohol function of the saccharide ring to the carboxylic acid function. Such oxidized dextrins and processes for their manufacture are known for example, from European Patent Applications EP 0232202 A1. A product oxidized at C6 of the saccharide ring can be particularly advantageous.

Oxydisuccinates and other derivatives of disuccinates, preferably ethylenediamine disuccinate are also further suitable cobuilders. Here, ethylene diamine-N,N'-disuccinate (EDDS), the synthesis of which is described for example, in U.S. Pat. No. 3,158,615, is preferably used in the form of its sodium or magnesium salts. In this context, glycerine disuccinates and glycerine trisuccinates are also particularly preferred, such as those described in U.S. Pat. No. 4,524, 009. Suitable addition quantities in zeolite-containing and/or silicate-containing formulations range from 3 to 15% by weight.

(Lactones. Other useful organic co-builders are, for example, acetylated hydroxycarboxylic acids and salts thereof which optionally may also be present in lactone form and which contain at least 4 carbon atoms, at least one hydroxyl group and at most two acid groups. Such cobuilders are described, for example, in International Patent Application WO 1995 020029 A1.

Bleaching Compounds, Bleaching Agents and Bleach Activators

The detergent compositions herein can optionally contain bleaching agents or bleaching compositions containing a bleaching agent and one or more bleach activators. When present, bleaching agents will typically be at levels of from about 1% to about 30%, more typically from about 5% to about 20%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches as well as other bleaching agents. Perborate bleaches, e.g., sodium perborate (e.g., mono- or tetra-hydrate) can be used herein.

Another category of bleaching agent that can be used without restriction encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONEO®, manufactured commercially by DuPont) can also be used.

A preferred percarbonate bleach comprises dry particles having an average particle size in the range from about 500 micrometers to about 1,000 micrometers, not more than about 10% by weight of said particles being smaller than about 200 micrometers and not more than about 10% by weight of said particles being larger than about 1,250 micrometers. Optionally, the percarbonate can be coated with silicate, borate or water-soluble surfactants. Percarbonate is available from various commercial sources.

Mixtures of bleaching agents can also be used.

Peroxygen bleaching agents, the perborates, the percarbonates, etc., are preferably combined with bleach activators, which lead to the in situ production in aqueous solution (i.e., during the washing process) of the peroxy acid corresponding to the bleach activator. The nonanoyloxybenzene sulfonate (NOBS) and tetraacetyl ethylene diamine (TAED) activators are typical, and mixtures thereof can also be used. Preferred amido-derived bleach activators include (6-octanamido-caproyl)oxybenzene-sulfonate, (6-nonanamido-caproyl)oxybenzenesulfonate, (6-decanamidocaproyl)oxyben-zenesulfonate, and mixtures thereof.

Another class of bleach activators comprises the benzoxazin-type activators disclosed in U.S. Pat. No. 4,966,723, incorporated herein by reference.

Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof, optionally adsorbed into solid carriers, e.g acyl caprolactams, preferably benzoyl caprolactam, adsorbed into sodium perborate.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. If used, detergent compositions will typically contain from about 0.025% to about 1.25%, by weight, of such bleaches, especially sulfonate zinc phthalocyanine.

If desired, the bleaching compounds can be catalyzed by means of a manganese compound. Such manganese-based catalysts are well known in the art and include $Mn^{IV}_2$ $(u-O)_3$ (1,4,7-trimethyl-1,4,7-triazacyclononane)$_2$ $(PF_6)_2$, $Mn^{III}_2$ $(u-O)_1$ $(u-OAc)_2$ (1,4,7-trimethyl-1,4,7-triazacyclononane)$_2$ $(ClO_4)_2$, $Mn^{IV}_4$ $(u-O)_6$ (1,4,7-triazacyclononane)$_4$ $(ClO_4)_4$, $Mn^{III}Mn^{IV}_4$ $(u-O)_1$ $(u-OAc)_2$ (1,4,7-trimethyl-1,4,7-triazacyclononane)$_2$ $(ClO_4)_3$, $Mn^{IV}$ (1,4,7-trimethyl-1,4,7-triazacyclononane)-$(OCH_3)_3(PF_6)$, and mixtures thereof.

As a practical matter, and not by way of limitation, the compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 500 ppm, of the catalyst species in the laundry liquor.

Polymeric Soil Release Agents

Any polymeric soil release agent known to those skilled in the art can optionally be employed in the detergent compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and, thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate: $C_3$ oxyalkylene terephthalate units is about 2:1 or lower, (ii) $C_4$-$C_6$ alkylene or oxy $C_4$-$C_6$ alkylene segments, or mixtures therein, (iii) poly (vinyl ester) segments, preferably polyvinyl acetate), having a degree of polymerization of at least 2, or (iv) $C_1$-$C_4$ alkyl ether or $C_4$ hydroxyalkyl ether substituents, or mixtures therein, wherein said substituents are present in the form of $C_1$-$C_4$ alkyl ether or $C_4$ hydroxyalkyl ether cellulose derivatives, or mixtures therein, and such cellulose derivatives are amphiphilic, whereby they have a sufficient level of $C_1$-$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a) (i) will have a degree of polymerization of from about 200, although higher levels can be used, preferably from 3 to about 150, more preferably from 6 to about 100. Suitable oxy $C_4$-$C_6$ alkylene hydrophobe segments include, but are not limited to, end-caps of polymeric soil release agents.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL® (Dow). Cellulosic soil release agents for use herein also include those selected from the group consisting of $C_1$-$C_4$ alkyl and $C_4$ hydroxyalkyl cellulose.

Soil release agents characterized by poly(vinyl ester) hydrophobe segments include graft copolymers of poly (vinyl ester), e.g., $C_1$-$C_6$ vinyl esters, preferably poly(vinyl acetate) grafted onto polyalkylene oxide backbones, such as polyethylene oxide backbones, see EP 0 219 048, incorporated herein in its entirety. Commercially available soil release agents of this kind include the SOKALAN® type of material, e.g., SOKALAN® HP-22, available from BASF.

One type of preferred soil release agent is a copolymer having random blocks of ethylene terephthalate and polyethylene oxide (PEO) terephthalate. The molecular weight of this polymeric soil release agent preferably is in the range of from about 25,000 to about 55,000.

Another preferred polymeric soil release agent is a polyester with repeat units of ethylene terephthalate units contains 10-15% by weight of ethylene terephthalate units together with 90-80% by weight of polyoxyethylene terephthalate units, derived from a polyoxyethylene glycol of average molecular weight 300-5,000. Examples of this polymer include the commercially available material ZELCON® 5126 (from DuPont) and MILEASE® T (from ICI).

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451. Other suitable polymeric soil release agents include the terephthalate polyesters of U.S. Pat. No. 4,711,730, the anionic end-capped oligomeric esters of U.S. Pat. No. 4,721,580, the block polyester oligomeric compounds of U.S. Pat. No. 4,702,857, and anionic, especially sulfoaroyl, end-capped terephthalate esters of U.S. Pat. No. 4,877,896 all cited patents incorporated herein in their entirety.

Still another preferred soil release agent is an oligomer with repeat units of terephthaloyl units, sulfoisoterephthaloyl units, oxyethyleneoxy and oxy-1,2-propylene units. The repeat units form the backbone of the oligomer and are preferably terminated with modified isethionate end-caps. A particularly preferred soil release agent of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. Said soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

If utilized, soil release agents will generally comprise from about 0.01% to about 10.0%, by weight, of the detergent compositions herein, typically from about 0.1% to about 5%, preferably from about 0.2% to about 3.0%.

Polymeric Dispersing Agents

Polymeric dispersing agents can advantageously be utilized at levels from about 0.1% to about 7%, by weight, in the detergent compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid. Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example U.S. Pat. No. 3,308,067.

Acrylic/maleic-based copolymers can also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000, more preferably from about 5,000 to 75,000, most preferably from about 7,000 to 65,000. The ratio of acrylate to maleate segments in such copolymers will generally range from about 30:1 to about 1:1, more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in EP 0193360 A1, which also describes such polymers comprising hydroxypropylacrylate. Still other useful dispersing agents include the maleic/acrylic/vinyl alcohol terpolymers, for example, a 45/45/10 terpolymer of acrylic/maleic/vinyl alcohol.

Another polymeric material which can be included is polyethylene glycol (PEG). PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000.

Polyaspartate and polyglutamate dispersing agents can also be used, especially in conjunction with zeolite builders. Dispersing agents such as polyaspartate preferably have a molecular weight (avg.) of about 10,000.

Foam Inhibitors/Sud Supressors

Especially when used in automatic washing processes, it can be advantageous to add conventional foam inhibitors to the compositions. Suitable foam inhibitors include for example, soaps of natural or synthetic origin, which have a high content of $C_{18}$-$C_{24}$ fatty acids. Suitable non-surface-active types of foam inhibitors are, for example, organopolysiloxanes and mixtures thereof with microfine, optionally silanised silica and also paraffins, waxes, microcrystalline waxes and mixtures thereof with silanised silica or bis-stearyl ethylenediamide. Mixtures of various foam inhibitors, for example, mixtures of silicones, paraffins or waxes, are also used with advantage. Preferably, the foam inhibitors, especially silicone-containing and/or paraffin-containing foam inhibitors, are loaded onto a granular, water-soluble or dispersible carrier material. Especially in this case, mixtures of paraffins and bis-stearylethylene diamides are preferred.

Compounds for reducing or suppressing the formation of suds can be incorporated into the detergent compositions of the present invention. Suds suppression can be of particular importance in the so-called "high concentration cleaning process" and in front-loading European-style washing machines.

A wide variety of materials can be used as suds suppressors, and suds suppressors are well known to those skilled in the art. See, for example, Kirk Othmer Encyclopedia of Chemical Technology, Third Edition, Volume 7, pages 430-447 (John Wiley & Sons, Inc., 1979). One category of suds suppressor of particular interest encompasses monocarboxylic fatty acid and soluble salts therein. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The detergent compositions herein can also contain non-surfactant suds suppressors. These include, for example: high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), etc. Other suds inhibitors include N-alkylated amino triazines such as tri- to hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 50° C., and a minimum boiling point not less than about 110° C. (atmospheric pressure). It is also known to utilize waxy hydrocarbons, preferably having a melting point below about 100° C. Hydrocarbon suds suppressors are known in the art and include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressors are well known in the art.

Other silicone suds suppressors are disclosed in U.S. Pat. No. 3,455,839, incorporated herein in its entirety, which relates to compositions and processes for defoaming aqueous solutions by incorporating therein small amounts of polydimethylsiloxane fluids.

Mixtures of silicone and silanated silica are described, for instance, in DE-OS 2124526, incorporated herein in its entirety. Silicone defoamers and suds controlling agents in granular detergent compositions are disclosed in U.S. Pat. No. 4,652,392, incorporated herein in its entirety.

In the preferred silicone suds suppressor used herein, the solvent for a continuous phase is made up of certain polyethylene glycols or polyethylene-polypropylene glycol copolymers or mixtures thereof (preferred), or polypropylene glycol. The primary silicone suds suppressor is branched/crosslinked and preferably not linear.

The silicone suds suppressor herein preferably comprises polyethylene glycol and a copolymer of polyethylene glycol/polypropylene glycol, all having an average molecular weight of less than about 1,000, preferably between about 100 and 800. The polyethylene glycol and polyethylene/polypropylene copolymers herein have a solubility in water at room temperature of more than about 2 weight %, preferably more than about 5 weight %.

The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

The preferred silicone suds suppressors used herein do not contain polypropylene glycol, particularly of 4,000 molecular weight. They also preferably do not contain block copolymers of ethylene oxide and propylene oxide, like PLURONIC® L101.

Other suds suppressors useful herein comprise the secondary alcohols (e.g., 2-alkyl alkanols) and mixtures of such alcohols with silicone oils. The secondary alcohols include the $C_6$-$C_{16}$ alkyl alcohols having a $C_1$-$C_{16}$ chain. A preferred alcohol is 2-butyl octanol, which is available from Condea under the trademark ISOFOL® 12. Mixtures of secondary alcohols are available under the trademark ISALCHEM® 123 from Enichem. Mixed suds suppressors typically comprise mixtures of alcohol+silicone at a weight ratio of 1:5 to 5:1.

The compositions herein will generally comprise from 0% to about 5% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts can be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that can be utilized in combination with polyorganosiloxane, as well as any adjunct materials that can be utilized. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%-3% by weight of the finished compositions.

Sequestrants and Chelating Agents

The salts of polyphosphonic acid can be considered as sequestrants or as stabilizers, particularly for peroxy compounds and enzymes, which are sensitive towards heavy metal ions. Here, the sodium salts of, for example, 1-hydroxyethane-1,1-diphosphonate, diethylenetriamine pentamethylene phosphonate or ethylenediamine tetramethylene phosphonate are used in amounts of 0.1 to 5 wt. %.

The detergent compositions herein can also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates. It is understood that some of the detergent builders described hereinbefore can function as chelating agents and is such detergent builder is present in a sufficient quantity, it can provide both functions.

Amino carboxylates useful as optional chelating agents include ethylenediaminetetracetates, N-hydroxyethylethylenediaminetriacetates, nitrilotriacetates, ethylenediamine tetra proprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Clay Soil Removal/Anti-Redeposition Agents

The detergent compositions of the present invention can also optionally contain water-soluble ethoxylated amines having clay soil removal and antiredeposition properties. Granular detergent compositions which contain these compounds typically contain from about 0.01% to about 10.0% by weight of the water-soluble ethoxylates amines; liquid detergent compositions typically contain about 0.01% to about 5%.

The most preferred soil release and anti-redeposition agent is ethoxylated tetraethylenepentamine. Exemplary ethoxylated amines are further described in U.S. Pat. No. 4,597,898. Other groups of preferred clay soil removal-antiredeposition agents are the cationic compounds disclosed in EP 0111965 A1, the ethoxylated amine polymers disclosed in EP 0111984 A1, the zwitterionic polymers disclosed in EP 0112592 A1, and the amine oxides disclosed in U.S. Pat. No. 4,548,744. Another type of preferred antiredeposition agent includes the carboxy methyl cellulose (CMC) materials. These materials are well known in the art.

Graying Inhibitors

Graying inhibitors have the function of maintaining the dirt that was removed from the fibers suspended in the washing liquor, thereby preventing the dirt from resettling. Water-soluble colloids of mostly organic nature are suitable for this, for example, the water-soluble salts of (co)polymeric carboxylic acids, glue, gelatins, salts of ether carboxylic acids or ether sulfonic acids of starches or celluloses, or salts of acidic sulfuric acid esters of celluloses or starches. Water-soluble, acid group-containing polyamides are also suitable for this purpose. Moreover, soluble starch preparations and others can be used as the above-mentioned starch products, e.g., degraded starches, aldehyde starches etc. Polyvinyl pyrrolidone can also be used. Preference, however, is given to the use of cellulose ethers such as carboxymethyl cellulose (Na salt), methyl cellulose, hydroxyalkyl celluloses and mixed ethers such as methyl hydroxyethyl cellulose, methyl hydroxypropyl cellulose, methyl carboxymethyl cellulose and mixtures thereof, as well as polyvinyl pyrrolidone, which can be added, for example, in amounts of 0.1 to 5 wt. %, based on the composition.

Optical Brighteners And UV Adsorbers

Any optical brighteners or other brightening or whitening agents known in the art can be incorporated at levels typically from about 0.05% to about 1.2%, by weight, into the detergent compositions herein. Commercial optical brighteners which can be useful in the present invention can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents.

Preferred brighteners include the PHORWHITE® series of brighteners from Verona. Other brighteners disclosed in this reference include: Tinopal® UNPA, Tinopal CBS and Tinopal 5BM; available from Ciba-Geigy; Artic White® CC and Artic White CWD, available from Hilton-Davis; the 2-(4-stryl-phenyl)-2H-napthol [1,2-d]triazoles; 4,4'-bis-(1,2,3-triazol-2-yl)-stilbenes; 4,4'-bis(stryl)bisphenyls; and the aminocoumarins. Specific examples of these brighteners include 4-methyl-7-diethyl-amino coumarin; 1,2-bis(-venzimidazol-2-yl)ethylene; 1,3-diphenyl-phrazolines; 2,5-bis(benzoxazol-2-yl)thiophene; 2-stryl-napth-[1,2-d] oxazole; and 2-(stilbene-4-yl)-2H-naphtho-[1,2-d]triazole. Anionic brighteners are preferred herein.

The compositions may comprise e.g., derivatives of diaminostilbene disulfonic acid or alkali metal salts thereof as the optical brighteners. Suitable optical brighteners are, for example, salts of 4,4'-bis-(2-anilino-4-morpholino-1,3,5-triazinyl-6-amino)stilbene-2,2'-disulfonic acid or compounds of similar structure which contain a diethanolamino group, a methylamino group, an anilino group or a 2-methoxyethylamino group instead of the morpholino group. Brighteners of the substituted diphenylstyryl type may also be present, for example, the alkali metal salts of 4,4'-bis(2-sulfostyryl)diphenyl, 4,4'-bis(4-chloro-3-sulfostyryl)diphenyl or 4-(4-chlorostyryl)-4'-(2-sulfostyryl) diphenyl. Mixtures of the mentioned brighteners may also be used.

In addition, UV absorbers may also be added. These are compounds with distinct absorption abilities for ultra violet radiation, which contribute as UV stabilizers as well as to improve the light stability of colorants and pigments both for textile fibers as well as for the skin of the wearer of textile products by protecting against the UV radiation that penetrates the fabric. In general, the efficient radiationless deactivating compounds are derivatives of benzophenone, substituted with hydroxyl and/or alkoxy groups, mostly in position(s) 2 and/or 4. Also suitable are substituted benzotriazoles, additionally acrylates that are phenyl-substituted in position 3 (cinnamic acid derivatives), optionally with cyano groups in position 2, salicylates, organic Ni complexes, as well as natural substances such as umbelliferone and the endogenous urocanic acid. In a preferred embodiment, the UV absorbers absorb UV-A and UV-B radiation as well as possible UV-C radiation and re-emit light with blue wavelengths, such that they additionally have an optical brightening effect. Preferred UV absorbers encompass triazine derivatives, e.g., hydroxyaryl-1,3,5-triazine, sulfonated 1,3,5-triazine, o-hydroxyphenylbenzotriazole and 2-aryl-2H-benzotriazole as well as bis(anilinotriazinyl-amino)stilbene disulfonic acid and their derivatives. Ultra violet absorbing pigments like titanium dioxide can also be used as UV absorbers.

Dye Transfer Inhibiting Agents

The detergent compositions of the present invention can also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein are described in U.S. Pat. No. 6,491,728, incorporated herein by reference.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide. The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000. This preferred class of materials can be referred to as "PVNO".

The most preferred polyamine N-oxide useful in the detergent compositions herein is poly(4-vinylpyridine-N-oxide) which as an average molecular weight of about 50,000 and an amine to amine N-oxide ratio of about 1:4.

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also can employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The detergent compositions herein can also optionally contain from about 0.005% to 5% by weight of certain types of hydrophilic optical brighteners which also provide a dye transfer inhibition action. If used, the compositions herein will preferably comprise from about 0.01% to 1% by weight of such optical brighteners.

One preferred brightener is 4,4'-bis[(4-anilino-6-(N-2-bis-hydroxyethyl)-s-triazine-2-yl)amino]-2,2'-stilbenedisulfonic acid and disodium salt. This particular brightener species is commercially marketed under the trade name Tinopal-UNPA-GX® by Ciba-Geigy Corporation. Tinopal-UNPA-GX is the preferred hydrophilic optical brightener useful in the detergent compositions herein.

Another preferred brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the trade name Tinopal 5BM-GX® by Ciba-Geigy Corporation.

Another preferred brightener brightener is 4,4'-bis[(4-anilino-6-morpholino-s-triazine-2-yl)amino]2,2'-stilbenedisulfonic acid, sodium salt. This particular brightener species is commercially marketed under the trade name Tinopal AMS-GX® by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX, Tinopal 5BM-GX and/or Tinopal AMS-GX) provides significantly better dye transfer inhibition in aqueous wash solutions than does either of these two detergent composition components when used alone. Without being bound by theory, it is believed that such brighteners work this way because they have high affinity for fabrics in the wash solution and therefore deposit relatively quick on these fabrics. The extent to which brighteners deposit on fabrics in the wash solution can be defined by a parameter called the "exhaustion coefficient". The exhaustion coefficient is in general as the ratio of a) the brightener material deposited on fabric to b) the initial brightener concentration in the wash liquor. Brighteners with relatively high exhaustion coefficients are the most suitable for inhibiting dye transfer in the context of the present invention.

Of course, it will be appreciated that other, conventional optical brightener types of compounds can optionally be used in the present compositions to provide conventional fabric "brightness" benefits, rather than a true dye transfer inhibiting effect. Such usage is conventional and well-known to detergent formulators.

Thickeners

The compositions can also comprise common thickeners and anti-deposition compositions as well as viscosity regulators such as polyacrylates, polycarboxylic acids, polysaccharides and their derivatives, polyurethanes, polyvinyl pyrrolidones, castor oil derivatives, polyamine derivatives such as quaternized and/or ethoxylated hexamethylenediamines as well as any mixtures thereof. Preferred compositions have a viscosity below 10,000 mPa*s, measured with a Brookfield viscosimeter at a temperature of 20° C. and a shear rate of 50 min$^{-1}$.

Inorganic Salts

Further suitable ingredients of the composition are water-soluble inorganic salts such as bicarbonates, carbonates, amorphous silicates or mixtures of these; alkali carbonate and amorphous silicate are particularly used, principally sodium silicate with a molar ratio Na$_2$O:SiO$_2$ of 1:1 to 1:4.5, preferably of 1:2 to 1:3.5. Preferred compositions comprise alkaline salts, builders and/or cobuilders, preferably sodium carbonate, zeolite, crystalline, layered sodium silicates and/or trisodium citrate, in amounts of 0.5 to 70 wt. %, preferably 0.5 to 50 wt. %, particularly 0.5 to 30 wt. % anhydrous substance.

Perfumes and Colorants

The compositions can comprise further typical detergent and cleansing composition ingredients such as perfumes and/or colorants, wherein such colorants are preferred that leave no or negligible coloration on the fabrics being washed. Preferred amounts of the totality of the added colorants are below 1 wt. %, preferably below 0.1 wt. %, based on the composition. The compositions can also comprise white pigments such as e.g., TiO$_2$.

INDUSTRIAL APPLICATION

Another object of the present invention refers to a method for improving the olfactory aspects and/or for preventing unpleasant olfactory aspects of a fragrance, comprising the step of providing a fragrance in need of olfactory support and applying at least one compound of formula (I) and at least one compound of formula (II) to said fragrance.

Finally, the invention also includes the use of the mixture of components (a), (b), (c) and optionally (d) for improving the olfactory aspects and/or for preventing unpleasant olfactory aspects of a fragrance As far the method and the use is related to specific combinations of species or their amounts reference is made to the explanations provided above which are applicable mutatis-mutandis without repeating them.

EXAMPLES

Example 1

121.6 g (−)-carveol (CAS 99-48-9), 30.8 g (−)-dihydrocarveol (CAS 20549-47-7) and 3 g sodium carbonate were placed in a 2-l three-necked flask equipped with KPG stirrer, dropping funnel and cooler and dissolved in 150 ml toluene. Subsequently, the mixture was heated and kept under reflux. Within one hour 112.2 g (1.1 mol) acetic anhydride were added dropwise and the reaction continued for another two hours at a temperature of 120 ° C. Once esterification was terminated the product was cooled down to about 75 to 80 ° C. and slowly subjected with 10 ml water. The organic phase thus obtained was washed with portions of 50 ml water, 50 ml sodium carbonate solution (5% b.w.) and sodium chloride solution (5% b.w.). Finally, the organic phase was removed under vacuum (70 ° C., 15 mbar). The remaining solid essentially consisted of [(1R,5R)-5-isopropenyl-2-methyl-cyclohex-2-en-1-yl]acetate and [(1R,5R)-5-isoproepnyl-2-methyl-cyclohexyl]acetate in a ratio by weight of 82.5:17.5.

Example 2

The following mixtures A, B and C were obtained by blending the components according to the following Table I.

TABLE I

| Fragrance compositions | | | |
|---|---|---|---|
| COMPOUNDS | A | B | C |
| AGRUNITRIL | 1.54 | 0.00 | 1.54 |
| ALLYLCAPRONAT | 0.03 | 0.00 | 0.03 |
| AMYLSALICYLAT | 0.01 | 0.00 | 0.01 |
| BHT JONOL | 0.10 | 0.00 | 0.10 |
| CINEOL 1,4 | 0.04 | 0.00 | 0.04 |
| CITRONELLOL | 0.13 | 0.00 | 0.13 |
| CITRONELLYLACETAT | 0.02 | 0.00 | 0.02 |
| CORTEX ALDEHYD 50 | 0.01 | 0.00 | 0.01 |
| DIHYDROMYRCENOL | 1.33 | 0.00 | 1.33 |
| DIPROPYLENGLYCOL | 0.83 | 0.00 | 0.83 |
| EUGENOL NAT. 10% DPG | 0.05 | 0.00 | 0.05 |
| FENCHOL 10% DPG | 0.01 | 0.00 | 0.01 |
| FLOROPAL | 0.02 | 0.00 | 0.02 |
| GERANIOL | 0.15 | 0.00 | 0.15 |
| GERANYLACETAT | 0.05 | 0.00 | 0.05 |
| HERBAFLORAT | 0.67 | 0.00 | 0.67 |
| HERBYLPROPIONAT | 0.05 | 0.00 | 0.05 |
| HEXYLACETAT | 0.67 | 0.00 | 0.67 |
| KAMPFEROL | 0.24 | 0.00 | 0.24 |
| LINALOOL | 0.72 | 0.00 | 0.72 |
| MANZANATE | 0.02 | 0.00 | 0.02 |
| METHYLHEPTENON-6,5,2 10% DPG | 0.02 | 0.00 | 0.02 |
| NEROLIN BROMELIA | 0.36 | 0.00 | 0.36 |
| ORANGE 20X BASE | 0.05 | 0.00 | 0.05 |
| ORANGENOEL BRAS. | 0.46 | 0.00 | 0.46 |
| STYROLYLACETAT | 0.29 | 0.00 | 0.29 |
| TERPINEOL ALPHA | 0.07 | 0.00 | 0.07 |

TABLE I-continued

Fragrance compositions

| COMPOUNDS | A | B | C |
|---|---|---|---|
| TERPINOLEN | 0.62 | 0.00 | 0.62 |
| VANILLIN 10% in DPG | 0.15 | 0.00 | 0.15 |
| GRAPEFRUITOL | 1.28 | 0.00 | 1.28 |
| PRODUCT ACCORDING EXAMPLE 1 | 0.00 | 0.02 | 0.02 |
| DIPROPYLEMGLYCOL | ad 100 | ad 100 | ad 100 |

Scent stripes were treated with the compositions A, B and C and scent intensity of certain olfactory aspects determined by a panel of experienced examiners using a scale from (0)=not to be detected to (10)=very strong. The results are compiled in Table II:

TABLE I

Olfactory aspects

| ASPECTS | A | B | C |
|---|---|---|---|
| bloomy | 5 | 0 | 7 |
| fruity | 3 | 0 | 5 |
| amber | 4 | 0 | 7 |
| ligneous | 2 | 0 | 5 |
| musky | 1 | 0 | 4 |
| metallic | 3 | 4 | 0 |
| oily | 2 | 4 | 0 |
| technical | 4 | 3 | 0 |
| onion-like | 0 | 5 | 0 |
| garlic-like | 0 | 4 | 0 |
| carbide | 0 | 1 | 0 |

Formulation Examples 1 to 66

TABLE 1

Liquid soap, transparent (Amounts in % b.w.)

| Ingredients | INCI Name | Amount |
|---|---|---|
| Tagat O 2 | PEG-20 Glyceryl Oleate | 2.5 |
| Coconut oil diethanolamine condensate | Cocamide DEA | 5.0 |
| Abil B 8842 | Cyclomethicone | 0.5 |
| Sodium laurylethersulfate. 28% | Sodium Laureth Sulfate | 35.0 |
| Tego-Betaine L7 | Cocamidopropyl Betaine | 5.0 |
| Soap. 25% | Coconut acid. Potassium salt. Potassium Oleate | 20.0 |
| Fragrance composition B | Fragrance | 0.4 |
| Preservative | DMDM Hydantoin | 0.2 |
| Water | Water | Ad 100 |

TABLE 2

Syndet soap, liquid (Amounts in % b.w.)

| Ingredients | INCI Name | Amount |
|---|---|---|
| Elfan OS 46 | Sodium Olefin C14-C16 Sulfonate | 35.5 |
| Armoteric LB | Lauryl Betaine | 8.0 |
| Elfan SG | | 10.0 |
| Elfacos GT 282 L | Talloweth-60 Myristyl Glycol | 3.0 |
| PCL-Liquid 100 | Cetearyl Ethylhexanoate | 4.0 |
| Fragrance composition B | Fragrance | 0.4 |
| Preservative | Methylchloroisothiazolinone. Methylisothiazinone | 0.1 |
| Water | Water | Ad 100 |

TABLE 3

Cosmetic lotion for body wash (Amounts in % b.w.)

| Ingredients | INCI Name | Amount |
|---|---|---|
| Lumerol K 28 | Disodium Laureth Sulfosuccinate. Cocamidopropyl Betaine. Magnesium Lauryl Sulfate | 33.0 |
| Amphotensid B 4 | Cocamidopropyl Betaine | 10.0 |
| Perlglanzmittel GM 4055 | MIPA-Pareth-25 Sulfate. Glycol Stearate | 4.0 |
| Sodium Chloride | Sodium Chloride | 2.0 |
| Avocado oil | *Persea Gratissima* (Avocado) Oil | 3.0 |
| Water | Water | Ad 100 |
| Fragrance composition B | Fragrance | 0.5 |
| Euxyl ® K727 | Phenoxyethanol. Methyldibromo Glutaronitrile. Isothiazolinones | 0.3 |

TABLE 4

Cosmetic lotion for body wash with Triclosan (Amounts in % b.w.)

| Ingredients | INCI Name | Amount |
|---|---|---|
| Texapon N 25 | Sodium Laureth Sulfate | 37.5 |
| Lamepon S | Potassium Cocoyl Hydrolyzed Collagen | 28.0 |
| Lamesoft LMG | Hydrogenated Tallow Glycerides. TEA-Cocoyl Hydrolyzed Collagen | 5.0 |
| Lamesoft 156 | Glyceryl Laurate. TEA-Cocoyl Hydrolyzed Collagen | 5.0 |
| Sodium Chloride | Sodium Chloride | 1.7 |
| Irgasan DP 300 | Triclosan | 0.5 |
| Water | Water | Ad 100 |
| Fragrance composition B | Fragrance | 0.3 |
| Euxyl ® K703 | Phenoxyethanol. Benzoic Acid. Dehydroacetic Acid | 0.4 |

TABLE 5

Intimate wash (Amounts in % b.w.)

| Ingredients | INCI Name | Amount |
|---|---|---|
| Tegobetaine HS | Cocamidopropyl Betaine. Glyceryl Laurate | 15.0 |
| Tagat L 2 | PEG-20 Glyceryl Laurate | 2.0 |
| Arlacide G | Chlorhexidine Digluconate | 0.1 |
| Rewoquat B 50 | Benzalkonium Chloride | 0.1 |
| Lactic Acid. 80% | Lactic Acid | 0.1 |
| Water | Water | Ad 100 |
| Fragrance composition B | Fragrance | 0.2 |
| Euxyl ® K700 | Potassium Sorbate. Benzyl Alcohol. Phenoxyethanol | 0.3 |

TABLE 6

Liquid soap (Amounts in % b.w.)

| Ingredient | INCI | Amount |
|---|---|---|
| Deionized water | Water | 2.0 |
| Soap bases mix | Sodium tallowates/palmitates | 95.8 |
| Titanium dioxide | Titanium dioxide | 1.0 |
| Fragrance composition B | Fragrance | 1.2 |
| Preservatives | Phenoxyethanol | 0.5 |
| Hydroxyacetophenone | Hydroxyacetophenone | 0.5 |

TABLE 7

Shampoo (Amounts in % b.w.)

| Ingredients | Amount |
| --- | --- |
| Sodium lauryl ether sulfate (e.g. Texapon NSO) | 12 |
| Cocamidopropyl betaine (e.g. Dehyton K) | 2 |
| Sodium chloride | 1.4 |
| Citric acid | 1.3 |
| Fragrance composition B | 0.3 |
| Phenoxyethanol. methyl-. ethyl-. butyl- and propylparaben | 0.5 |
| Water | Ad 100 |

TABLE 8

2-in-1 Shampoo (Amounts in % b.w.)

| Ingredients | INCI Name | Amount |
| --- | --- | --- |
| Deionized water | Water | Ad 100 |
| Plantacare PS 10 | Sodium Laureth Sulfate. Lauryl Glucoside | 20.0 |
| Euperlan PK 771 | Glycol Distearate. Sodium Lauryl Sulfate. Cocamide MEA. Laureth-10 | 6.0 |
| Sodium chloride | Sodium Chloride | 1.4 |
| Citric acid monohydrate crystalline | Citric acid | 0.1 |
| Fragrance composition B | Fragrance | 0.5 |
| Dragocid Liquid | Phenoxyethanol, Parabens | 0.5 |
| Hydroxyacetophenone | Hydroxyacetophenone | 0.5 |

TABLE 9

Anti-dandruff Shampoo (Amounts in % b.w.)

| Ingredients | Amount |
| --- | --- |
| Climbazole | 0.50 |
| Sodium Laureth Sulfate | 37.00 |
| Cocamidopropyl Betaine | 8.00 |

TABLE 9-continued

Anti-dandruff Shampoo (Amounts in % b.w.)

| Ingredients | Amount |
| --- | --- |
| PEG-6 Caprylic/Capric Glycerides | 2.50 |
| Laureth-2 | 2.00 |
| Water (Aqua). Glycerol. *Thymus Vulgaris* (Thyme). Flower/Leaf Extract | 0.50 |
| Bisabolol | 0.10 |
| Panthenol | 0.50 |
| Polyquaternium-10 | 0.40 |
| Fragrance composition B | 0.50 |
| Phenoxyethanol. Methylparaben. Ethylparaben. Butylparaben. Propylparaben. Iso-butylparaben | 0.70 |
| Water (Aqua) | Ad 100 |

TABLE 10

Hair conditioner with Crinipan. rinse-off (Amounts in % b.w.)

| Ingredients | INCI Name | Amount |
| --- | --- | --- |
| Lanette ® O | Cetearyl Alcohol | 4.00 |
| Dragoxat 89 | Ethylhexyl Isononanoate | 2.00 |
| Genamin ® KDM-P | Behentrimonium Chloride | 1.00 |
| SF 1550 | Phenyl Trimethicone | 0.10 |
| Neo Heliopan ® BB | Benzophenone-3 | 0.10 |
| Crinipan ® AD | Climbazole | 0.80 |
| Glycerol 99.5 P. | Glycerol | 6.00 |
| Water | Water (Aqua) | Ad 100 |
| Actipone ® Alpha Pulp | Water (Aqua). Butylene Glycol. Malic Acid. *Actinidia Chinensis* (Kiwi) Fruit Juice. *Citrus. Aurantium Dulcis* (Orange). Juice. *Citrus Paradisi* (Grapefruit) Juice. *Pyrus Malus* (Apple) Juice. Trideceth-9. *Prunus Amygdalus* Dulcis (Sweet Almond) Seed Extract | 0.50 |
| Extrapone ® Bamboo P | Propylene Glycol. Water (Aqua). Butylene Glycol. *Bambusa Vulgaris* Shoot Extract | 0.50 |
| Sodium Hydroxide 10% solution | Sodium Hydroxide | 0.40 |
| Colour I | Colour | 0.60 |
| Colour II | Colour | 0.30 |
| Fragrance composition B | Fragrance | 0.40 |
| Preservative | Methylparaben | 0.20 |

TABLE 11

Sprayable hair conditioner with zinc pyrithrione. leave-on (Amounts in % b.w.)

| Ingredients | INCI Name | Amount |
| --- | --- | --- |
| Monomuls 60-35 C | Hydrogenated Palm Glycerides | 1.70 |
| Cetiol OE | Dicaprylyl Ether | 7.20 |
| Abil 100 | Dimethicone | 3.60 |
| Dehyquart F 75 | Distearoylethyl Hydroxyethylmonium. Methosulfate. Cetearyl Alcohol | 4.00 |
| Eumulgin B1 | Ceteareth-12 | 3.50 |
| Cetiol S | Diethylhexylcyclohexane | 7.20 |
| D-Panthenol | Panthenol | 0.10 |
| Glycerol 99.5 P. | Glycerol | 1.50 |
| Water | Water (Aqua) | Ad 100 |
| Actipone ® Rosemary | Water (Aqua). Propylene. Glycol. *Rosmarinus Officinalis*. (Rosemary) Leaf Extract | 0.10 |
| Frescolat ® ML Cryst. | Menthyl Lactate | 0.50 |
| Dragosantol100 | Bisabolol | 0.10 |
| Zinc Omadine | Zinc pyrithione | 0.10 |
| Fragrance composition B | Fragrance | 0.40 |
| Phenonip ® | phenoxyethanol. methylparaben. ethylparaben. butylparaben. propylparaben. isobutylparaben | 0.30 |

TABLE 12

Hair conditioner with UV protection (Amounts in % b.w.)

| Ingredients | INCI Name | Amount |
|---|---|---|
| Reflex PEG 6000 | PEG-150 | 2.50 |
| Hair Conditioner Base | Cetyl alcohol. behentrimonium chloride. *Triticum Vulgare* (Wheat) bran extract. linoleic acid | 3.00 |
| PCL-Solid | Stearyl heptanoate. stearyl caprylate | 0.50 |
| Dow Corning 5200 | Laurylmethicone copolyol | 0.50 |
| Natrosol 250 HR | Hydroxyethylcellulose | 0.50 |
| Benzophenone-4 | Benzophenone-4 | 1.00 |
| Neo Heliopan AP | Disodiumphenyldibenz-imidazole tetrasulphonate | 1.00 |
| Amino methyl propanol | Amino methyl propanol | 2.00 |
| Dow Corning 949 cationic emulsion | Amodimethicone. cetrimonium chloride. trideceth-12 | 2.00 |
| Fragrance composition B | Fragrance | 0.80 |
| 1.2-hexanediol | 1.2-hexanediol | 0.50 |
| Hydroxyacetophenone | Hydroxyacetophenone | 0.50 |
| Water | Water (Aqua) | Ad 100 |

TABLE 13

Shower gel (Amounts in % b.w.)

| Ingredients | INCI | Amount |
|---|---|---|
| Deionized water | Water | Ad 100 |
| Plantacare PS 10 | Sodium Laureth Sulfate. Lauryl Glucoside | 20.0 |
| Sodium chloride | Sodium Chloride | 1.4 |
| Citric acid monohydrate crystalline | Citric Acid | 1.3 |
| Fragrance composition B | Fragrance | 0.6 |
| SymDiol ®68 | 1.2-hexanediol. caprylyl glycol | 0.4 |

TABLE 14

Shaving foam (Amounts in % b.w.)

| Ingredients | Amount |
|---|---|
| Dem. Water | 77.2 |
| Triethanolamine | 4.0 |
| Edenor L2 SM (Stearinic acid. Palmitinic acid) (Cognis) | 5.3 |
| Laureth-23 | 3.0 |
| Stearylalcohol | 0.5 |
| Sodium lauryl sulfate | 3.0 |
| Extrapone Seaweed (water. propylene glycol. potassium iodide. *Fucus Vesiculosus* Extract) | 1.0 |
| Dragosantol (Bisabolol. Farnesol) | 0.1 |
| Fragrance composition B | 1.0 |
| Euxyl ® K220 (Methylisothiazolinone. Ethylhexylglyerol) | 0.6 |
| Hydroxyacetophenone | 0.3 |
| Propane/Butane 4.2 Bar | 4.0 |

TABLE 15

Depilatory cream (Amounts in % b.w.)

| Ingredients | Amount |
|---|---|
| Cetearyl alcohol | 10.0 |
| Ceteareth-12 | 2.0 |
| PCL-Liquid (Cetearylethylhexanoate. Isopropylmyristate) | 3.0 |
| Dragosantol (Bisabolol. Farnesol) | 0.1 |
| Edenor L2 SM (Stearinic acid. Palmitinic acid) | 1.0 |
| Dem. Water | 52.2 |
| Urea | 5.0 |
| Dem. Water | 10.0 |
| Calcium thioglycolate | 6.0 |
| Sodium hydroxide solution. 10% | 10.0 |
| Fragrance composition B | 0.5 |
| Neo Dragocid Powder (Methyl parabene. sorbinic acid. Dehydro acetic acid. Propyl parabene) | 0.2 |
| Hydroxyacetophenone | 0.4 |

TABLE 16

After Shave Tonic (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 3.00 |
| SymSitive ® 1609 | Pentylene Glycol. 4-t-Butyl-cyclohexan ol | 1.00 |
| Frescolat ® ML | Menthyl Lactate | 0.30 |
| Glycerol 99.5 P. | Glycerol | 5.00 |
| Water | Water (Aqua) | Ad 100 |
| Extrapone ® Glacier Water GW | Glycerol. Water (Aqua) | 1.00 |
| SymCalmin ® | Butylene Glycol. Pentylene Glycol. Hydroxyphenyl Propamidobenzoic Acid | 0.50 |
| Dragosine ® | Carnosine | 0.10 |
| Hydrolite ® 5 | Pentylene Glycol | 5.00 |
| Ethanol 96% | Alcohol Denat. | 5.00 |
| Colour Pigment | Colour Pigment | 0.05 |
| Fragrance composition B | Fragrance | 0.15 |

TABLE 17

Deodorant formulation in the form of a roll-on gel (Amounts in % b.w.)

| Ingredients | Amount |
|---|---|
| 1.3-butylene glycol | 2.00 |
| PEG-40-hydrogenated castor oil | 2.00 |
| Hydroxyethylcellulose | 0.50 |
| Fragrance composition B | 0.30 |
| 1.3-propanediol | 0.50 |
| 3-phenylpropanol | 0.40 |
| Ethylhexyl glycerin | 0.10 |
| Water | ad 100.00 |

TABLE 18

Clear deo anti-perspirant roll-on (Amounts in % b.w.)

| Ingredients | INCI | Amount |
|---|---|---|
| Methocel E4M Premium | Hydroxypropyl Methylcellulose | 0.50 |
| Water | Water (Aqua) | Ad 100 |
| Neo-PCL Water Soluble N | Trideceth-9. PEG-5 Ethylhexanoate. Water (Aqua) | 1.00 |
| Solubilizer | PEG-40 Hydrogenated Castor Oil. Trideceth-9. Propylene Glycol. Water (Aqua) | 3.00 |
| Deolite | Dimethyl Phenylpropanol. Pentylene Glycol | 0.50 |
| Locron LW | Aluminium Chlorohydrate | 25.00 |
| Aloe Vera Gel Concentrate 10/1 | *Aloe Barbadensis* Leaf Juice | 1.00 |
| Propylene Glycol-1.2 99 P GC | Propylene Glycol | 4.00 |

TABLE 18-continued

Clear deo anti-perspirant roll-on (Amounts in % b.w.)

| Ingredients | INCI | Amount |
|---|---|---|
| Ethanol 96% | Alcohol Denat. | 30.00 |
| Fragrance composition B | Fragrance | 1.00 |

TABLE 19

Deodorant stick (Amounts in % b.w.)

| Ingredients | Amount |
|---|---|
| Sodium stearate | 8.00 |
| PPG-3 Myristyl ether | 70.00 |
| 1.2-propylene glycol | 10.00 |
| 1.1-dimethyl-3-phenylpropanol | 0.20 |
| 2-butyloctanoic acid | 0.20 |
| Fragrance composition B | 0.60 |
| Heptoxy-1.2-propanediol | 0.20 |
| Phenoxyethanol | 0.30 |
| Water | Ad 100 |

TABLE 20

Zirconium suspensoid antiperspirant stick (Amounts in % b.w.)

| Ingredients | INCI | Amount |
|---|---|---|
| PCL Liquid 100 | Cetearyl ethylhexanonate | to 100 |
| Silicone Fluid 345 | Cyclomethicone | 10.00 |
| CRODACOL C90 | Cetyl Alcohol | 8.00 |
| SYNCROWAX HGLC | C18-36 Triglyceride | 8.00 |
| CRODAMOL PTC | Pentaerythritol Tetracaprylate/Caprate | 5.00 |
| SYNCROWAX HRC | Tribehenin | 4.00 |
| VOLPO N5 | Oleth-5 | 1.00 |
| Titanium Dioxide | | 1.00 |
| Rezal 36GP | Aluminium Tetrachlorohydrex GLY | 20.00 |
| Dry Flo C | Aluminium Starch Octenyl Succinate | 22.50 |
| Fragrance composition B | Fragrance | 0.60 |
| Preservative | Phenoxyethanol | 0.40 |
| Hexoxy-1.2-propanediol | | 0.10 |
| Substance of formula (I) | Hydroxyacetophenone | 0.40 |

TABLE 21

Deodorant pump spray with SymClariol (Amounts in % b.w.)

| Ingredients | INCI | Amount |
|---|---|---|
| SymClariol ® | Decylene Glycol | 0.50 |
| Solubilizer | PEG-40 Hydrogenated Castor Oil. Trideceth-9. Propylene Glycol. Water (Aqua) | 4.00 |
| Neo-PCL Water Soluble N | Trideceth-9. PEG-5 Ethylhexanoate. Aqua | 1.50 |
| SymRelief ® | Bisabolol. Zingiber Officinale (Ginger) Root Extract | 0.10 |
| Water | Water (Aqua) | Ad 100 |
| 1.2 Propylene Glycol | Propylene Glycol | 6.00 |
| Fragrance composition B | Fragrance | 0.40 |
| SymDiol ® 68 | 1.2-Hexanediol. Caprylyl Glycol | 0.20 |

TABLE 22

Antiperspirant formulations (Amounts in % b.w.)

| Ingredients | Amounts |
|---|---|
| Reach AZP-908 SUF | 24.00 |
| Cyclomethicone (Pentamer) | Ad 100 |

TABLE 22-continued

Antiperspirant formulations (Amounts in % b.w.)

| Ingredients | Amounts |
|---|---|
| Polydecene (Silkflo 364 NF) | 17.50 |
| Neo Heliopan OS (ethylhexyl salicylate) | 2.50 |
| L-Menthyl lactate (Frescolate ML) | 0.25 |
| Polyethylene | 3.00 |
| Hydrogenated castor oil | 2.00 |
| Promyristyl PM-3 | 7.00 |
| PEG-8 Distearate | 3.00 |
| Silicon dioxide (Cab-O-Sil M-5) | 1.00 |
| Stearyl alcohol | 15.00 |
| Octyldodecanol | 0.10 |
| Fragrance composition B | 0.80 |
| 3-Phenylpropanol | 0.40 |
| Substance of formula (I) | 0.60 |

TABLE 23

Deodorant spray with Triclosan (Amounts in % b.w.)

| Ingredients | Amount |
|---|---|
| PEG-40-hydrogenated castor oil | 3.00 |
| Ethylhexylglycerol (Octoxyglycerol) | 0.80 |
| Ethanol | 40.00 |
| Citrate buffer | 0.50 |
| 1.2-Hexanediol/1.2-octanediol (1:1) | — |
| Triclosan ® (5-chloro-2-(2.4-dichlorophenoxy)phenol) | 0.25 |
| 2-Benzylheptan-1-ol (Jasmol) | — |
| Fragrance composition B | 0.75 |
| Phenoxyethanol | 0.40 |
| Water | Ad 100 |

TABLE 24

O/W lotion (Amounts in % b.w.)

| Ingredients | Amount |
|---|---|
| Paraffin oil | 5.00 |
| Isopropyl palmitate | 5.00 |
| Cetyl alcohol | 2.00 |
| Beeswax | 2.00 |
| Ceteareth-20 | 2.00 |
| PEG-20-glyceryl stearate | 1.50 |
| Glycerol | 3.00 |
| Fragrance composition B | 0.30 |
| Methylparaben | 0.30 |
| Water | ad 100.00 |

TABLE 25

Body lotion (Amounts in % b.w.)

| Ingredients | Amount |
|---|---|
| Cetearyl Alcohol | 2.00 |
| Ethylhexyl Isononanoate | 5.00 |
| Cetearyl Ethylhexanoate. Isopropyl Myristate | 3.00 |
| Glyceryl Oleate Citrate. Caprylic/Capric Triglyceride | 4.00 |
| Water (Aqua) | 79.50 |
| Carbomer | 0.30 |
| Sodium Benzoate | 0.100 |
| Propylene Glycol | 5.00 |
| Sodium Hydroxide 30% solution | 0.30 |
| Fragrance composition B | 0.30 |
| Triethylene Glycol. Imidazolidinyl Urea. Methylparaben. Propylparaben. Dehydroacetic Acid | 0.30 |
| Hydroxyacetophenone | 0.20 |

TABLE 26

Cream (Amounts in % b.w.)

| Ingredients | Amount |
|---|---|
| Paraffin oil | 10.00 |
| Ozokerite | 4.00 |
| Vaseline | 4.00 |
| Vegetable oil | 10.00 |
| Wool wax alcohol | 2.00 |
| Aluminium stearate | 0.40 |
| Fragrance composition B | 0.70 |
| 1.2-pentanediol | 2.00 |
| Phenoxyethanol | 0.50 |
| Water | ad 100.00 |

TABLE 27

Cream (Amounts in % b.w.)

| Ingredients | INCI | Amount |
|---|---|---|
| Dracorin ® CE | Glyceryl Stearate Citrate | 1.00 |
| Lanette ® O | Cetearyl Alcohol | 2.00 |
| Cutina ® GMS-V | Glyceryl Stearate | 1.00 |
| Tegosoft ® MM | Myristyl Myristate | 1.00 |
| Xiameter ® PMX-0246. Cyclosiloxane | Cyclohexasiloxane (and) Cyclopentasiloxane | 0.50 |
| Dragoxat ® 89 | Ethylhexyl Isononanoate | 2.00 |
| PCL-Liquid 100 | Cetearyl Ethylhexanoate | 4.00 |
| Neutral Oil | Caprylic/Capric Triglyceride | 4.00 |
| Carbopol ® Ultrez 21 | Acrylates/C10-30 Alkyl Acrylate Crosspolymer | 0.20 |
| Keltrol ® CG-T | Xanthan Gum | 0.10 |
| Water | Water (Aqua) | Ad 100 |
| Glycerol 99.5 P. | Glycerol | 3.00 |
| Propylene Glycol-1.2 99 P GC | Propylene Glycol | 2.00 |
| Sodium Benzoate | Sodium Benzoate | 0.10 |
| Sodium Hydroxide 10% solution | Sodium Hydroxide | 0.50 |
| Fragrance composition B | Perfume | 0.30 |
| Euxyl ® K702 | Dehydroacetic Acid. Benzoic Acid. Phenoxyethanol. Polyaminopropyl Biguanide. Ethylhexylglycerin | 0.30 |
| 4-hydroxyacetophenone | Hydroxyacetophenone | 0.70 |

TABLE 28

Hand and body cream (Amounts in % b.w.)

| Ingredients | INCI | Amount |
|---|---|---|
| Dracorin ® GOC | Glyceryl Oleate Citrate. Caprylic/Capric Triglyceride | 2.00 |
| PCL-Solid | Stearyl Heptanoate. Stearyl Caprylate | 2.50 |
| Lanette ® O | Cetearyl Alcohol | 1.50 |
| Cutina ® GMS-V | Glyceryl Stearate | 1.00 |
| Dragoxat ® 89 | Ethylhexyl Isononanoate | 3.00 |
| PCL-Liquid 100 | Cetearyl Ethylhexanoate | 7.00 |
| Isodragol ® | Triisononanoin | 4.00 |
| Xiameter ® PMX-0345 Cyclosiloxane | Cyclopentasiloxane (and) Cyclohexasiloxane | 0.50 |
| Water | Water (Aqua) | Ad 100 |
| Carbopol ® Ultrez 21 | Acrylates/C10-30 Alkyl Acrylate Crosspolymer | 0.20 |
| Keltrol ® CG-RD | Xanthan Gum | 0.10 |
| Glycerol 85 P. | Glycerol | 3.00 |
| DragoBetaGlucan | Water (Aqua). Butylene Glycol. Glycerol. *Avena Sativa* (Oat) Kernel Extract | 1.50 |
| Potassium Sorbat | Potassium Sorbate | 0.10 |
| Sodium Hydroxide 10% solution | Sodium Hydroxide | 0.50 |
| Fragrance composition B | Parfum | 0.20 |
| Euxyl ® K300 | Methyl-. Butyl-. Ethyl-. Propyl. Isobutylparaben. Phenoxyethanol. | 0.30 |
| 4-Hydroxyacetophenone | Hydroxyacetophenone | 0.30 |

TABLE 29

Face cream (Amounts in % b.w.)

| Ingredients | INCI | Amount |
|---|---|---|
| Emulsiphos ® | Potassium Cetyl Phosphate. Hydrogenated Palm Glycerides | 1.50 |

TABLE 29-continued

Face cream (Amounts in % b.w.)

| Ingredients | INCI | Amount |
|---|---|---|
| Cutina ® GMS-V | Glyceryl Stearate | 1.70 |
| Lanette ® O | Cetearyl Alcohol | 3.00 |
| Tegosoft ® MM | Myristyl Myristate | 1.00 |
| PCL-Liquid 100 | Cetearyl Ethylhexanoate | 1.00 |
| Isodragol ® | Triisononanoin | 3.00 |
| Dragoxat ® 89 | Ethylhexyl Isononanoate | 4.00 |
| Avocado Oil | *Persea Gratissima* (Avocado) Oil | 3.00 |
| Abil ® 350 | Dimethicone | 0.50 |
| Covi-ox ® T-70 | Tocopherol | 0.10 |
| Edeta ® BD | Disodium EDTA | 0.10 |
| Carbopol ® Ultrez 21 | Acrylates/C10-30 Alkyl Acrylate Crosspolymer | 0.30 |
| Keltrol ® CG-RD | Xanthan Gum | 0.150 |
| Water | Water (Aqua) | Ad 100 |
| Glycerol 99.5 P. | Glycerol | 4.00 |
| Propylene Glycol-1.2 99 P GC | Propylene Glycol | 3.00 |
| SymMatrix ® | Maltodextrin. *Rubus Fruticosus* (Blackberry) Leaf Extract | 0.50 |
| Sodium Hydroxide 10% solution | Sodium Hydroxide | 0.50 |
| Fragrance composition B | Parfum | 0.30 |
| Euxyl ® K712 | Sodium Benzoate. Potassium Sorbate | 0.20 |
| 4-Hydroxyacetophenone | Hydroxyacetophenone | 0.60 |

TABLE 30

Moisturizing body care cream (Amounts in % b.w.)

| Ingredient | Amount |
|---|---|
| PEG-7 hydrogenated castor oil | 6.00 |
| Cetearyl ethyl hexanoate | 10.00 |
| Isopropyl myristate | 5.00 |
| Mineral oil | 7.00 |
| Shea Butter (*Butyrospermum parkii*) | 0.50 |
| Aluminum stearate | 0.50 |
| Magnesium stearate | 0.50 |
| Bisabolol | 0.20 |
| Quaternium-18-Hectorit | 0.70 |
| Dipropylene glycol | 5.0 |
| Magnesium sulfate | 0.70 |
| Pentylene glycol | 4.00 |
| Fragrance composition B | 0.30 |
| Preservative (Phenoxyethanol) | 0.20 |
| Hydroxyacetophenone | 0.40 |
| Aqua dem. | 58.90 |

TABLE 31

Anti-wrinkle cream (Amounts in % b.w.)

| Ingredients | Amount |
|---|---|
| Glyceryl Stearate Citrate | 1.00 |
| Glyceryl Laurate | 1.00 |
| Cetearyl Alcohol (and) Myristyl Myristate | 3.00 |
| Cetearyl Ethylhexanoate | 4.00 |
| Mineral oil | 4.00 |
| Cyclopentasiloxane/Cyclohexasiloxane | 0.50 |
| Acrylates/C10-30 Alkyl Acrylate Crosspolymer | 0.20 |
| Water | Ad 100 |
| 1.2-Hexanediol | 2.00 |
| Sodium Hydroxide 10% solution | 0.10 |
| *Narcissus Tazetta* Bulb Extract | 1.00 |
| Fragrance composition B | 0.30 |
| Preservative (Phenoxyethanol) | 0.50 |

TABLE 32

Functional skin oil for disinfection (Amounts in % b.w.)

| Ingredients | INCI | Amount |
|---|---|---|
| Neutral Oil | Caprylic/Capric Triglyceride | Ad 100 |
| Sweet Almond Oil | *Prunus Dulcis* | 20.00 |
| Dragoxat ® 89 | Ethylhexyl Isononanoate | 4.00 |
| Isopropyl Palmitate | Isopropyl Palmitate | 6.00 |
| PCL-Liquid 100 | Cetearyl Ethylhexanoate | 15.00 |
| Dragosantol ® 100 | Bisabolol | 0.20 |
| Retinyl Acetate In Oil (1 Mio. le/G) | Retinyl Acetate | 0.50 |
| Vitamin E Acetate | Tocopheryl Acetate | 0.50 |
| Covi-ox ® T-70 | Tocopherol | 0.10 |
| Fragrance composition B | Parfum | 0.30 |
| Preservative | Methyl-. Butyl-. Ethyl-. Propylparaben | 0.30 |
| 4-hydroxyacetophenone | Hydroxyacetophenone | 0.40 |

TABLE 33

Septic wound cream (Amounts in % b.w.)

| Ingredients (INCI) | Amount |
|---|---|
| Sorbitan Isostearate. Hydrogenated Castor Oil. Ceresin. Beeswax (Cera Alba) | 6.00 |
| Petrolatum | 21.00 |
| Cera Alba | 5.00 |
| Cetearyl Alcohol | 7.00 |
| Prunus Dulcis | 7.00 |
| Lanolin | 5.00 |
| Paraffinum Liquidum | 12.00 |
| Fragrance composition B | 0.30 |
| Water (Aqua) | Ad 100 |
| Panthenol | 7.00 |
| Magnesium Sulfate | 0.70 |
| Pentylene Glycol | 1.00 |
| Tocopheryl Acetate | 1.00 |
| Octenidine dihydrochloride | 0.10 |
| Phenoxyethanol | 0.50 |

TABLE 34

Moisturizing and disinfecting face mask (Amounts in % b.w.)

| Ingredients | INCI | Amount |
|---|---|---|
| Water | Water (Aqua) | Ad 100 |
| Stabileze QM | PVM/Ma Decadiene Crosspolymer | 0.50 |
| Biotive ® L-Arginine | Arginine | 0.75 |
| Actipone ® Laminaria Saccharina GW | Glycerol. Water (Aqua). *Laminaria Saccharina* Extract | 1.00 |
| Extrapone ® Cucumber | Water (Aqua). Propylene Glycol. *Cucumis Sativus* (Cucumber) Juice | 1.00 |
| Glycerol 99.5 P. | Glycerol | 7.00 |
| Neo Actipone ® Soap Nutshell | *Sapindus Mukurossi* Peel Extract | 0.50 |
| Colour I | Colour | 0.01 |
| Hydrolite ® 5 | Pentylene Glycol | 5.00 |
| Solubilizer | PEG-40 Hydrogenated Castor Oil. Trideceth-9. Water (Aqua) | 0.60 |
| Fragrance composition B | Parfum | 0.08 |
| Preservative | Phenoxyethanol | 0.40 |
| 4-hydroxyacetophenone | Hydroxyacetophenone | 0.40 |

TABLE 35

Sprayable disinfecting gel (Amounts in % b.w.)

| Ingredients | INCI | Amount |
|---|---|---|
| Water | Water (Aqua) | Ad 100 |
| Stabileze QM | PVM/Ma Decadiene Crosspolymer | 0.25 |
| Sodium Hydroxide 10% solution | Sodium Hydroxide | 0.40 |
| Coffein pure | Caffeine | 0.50 |
| Extrapone ® Horse Chestnut | Propylene Glycol. Water (Aqua). Glucose. *Aesculus Hippocastanum* (Horse Chestnut) Seed Extract. Lactic Acid | 1.00 |
| Hydrolite ® 5 | Pentylene Glycol | 3.00 |
| 1.3 Butylene Glycol | Butylene Glycol | 5.00 |
| Biotive ® Esculin Sesquihydrate | Esculin | 0.30 |
| Ethanol 96% | Alcohol Denat. | 10.00 |
| Solubilizer | PEG-40 Hydrogenated Castor Oil. Trideceth-9. Water (Aqua) | 0.50 |
| Fragrance composition B | Parfum | 0.20 |
| Octenidine dihydrochloride | | 0.10 |
| Preservative | Phenoxyethanol | 0.70 |
| 4-hydroxy-acetophenone | Hydroxyacetophenone | 0.30 |

TABLE 36

Mineral wash and cleaning gel (Amounts in % b.w.)

| Ingredients | INCI | Amount |
|---|---|---|
| Water | Water (Aqua) | Ad 100 |
| Pionier ® NP 37 G | Sodium Carbomer | 1.50 |
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 5.00 |
| Hydroviton ® 24 | Water (Aqua). Pentylene Glycol. Glycerol. Sodium Lactate. Lactic Acid. Serine. Urea. Sorbitol. Sodium Chloride. Allantoin | 1.00 |
| Extrapone ® Silk GW | Water (Aqua). Glycerol. Hydrolyzed Silk | 1.00 |
| Hydrolite ® 5 | Pentylene Glycol | 4.00 |
| Actipearls Red Star # DH10402/6 | Water (Aqua). Propylene Glycol. Algin. Gellan Gum. Xanthan Gum. CalciumChloride. CI 12490 (Pigment Red 5). Mica (CI 77019). Titanium Dioxide (CI 77891) | 1.00 |
| Fragrance composition B | Parfum | 0.50 |
| 3-Phenyl-propanol | | 0.70 |
| 4-hydroxy-acetophenone | Hydroxyacetophenone | 0.30 |

TABLE 37

Anti-acne wash (Amounts in % b.w.)

| Ingredients (INCI) | Amount |
|---|---|
| Water (Aqua) | 45.70 |
| Polyquaternium-7 | 0.50 |
| Cocamidopropyl Betaine 9.000 | 9.00 |
| Coco Glucoside 2.000 | 2.00 |
| Polysorbate 80. Glycerol. *Gossypium Herbaceum*. (Cotton) Seed Oil. Water (Aqua) | 1.00 |
| Trideceth-9. PEG-5 Ethylhexanoate. Water (Aqua) | 1.00 |
| Glycereth-90 Isostearate. Laureth-2 | 0.50 |
| Sodium Laureth Sulfate 37.000 | 37.00 |

TABLE 37-continued

Anti-acne wash (Amounts in % b.w.)

| Ingredients (INCI) | Amount |
|---|---|
| Glycerol. *Triticum Vulgare* (Wheat) Gluten. | 1.00 |
| Water (Aqua) | |
| Sodium Chloride | 0.30 |
| Fragrance composition B | 1.00 |
| Phenoxyethanol. Methylparaben. Ethylparaben. Butylparaben. Propylparaben. Isobutylparaben | 0.30 |
| Substance of formula (I) | 0.50 |

TABLE 38

Cosmetic sun protection composition (Amounts in % b.w.)

| Ingredient | Amount |
|---|---|
| Ethylhexyl cinnamic acid | 7.50 |
| Benzophenon-3 | 2.00 |
| Polyglyceryl dimer soyate | 0.80 |
| Sorbitane stearate | 1.00 |
| Tocopheryl acetate | 0.50 |
| Glyceryl stearate. PEG-100 Stearate | 3.00 |
| PEG-40. hydrogenated castor oil | 1.00 |
| Titanium dioxide. aluminum oxide hydrate. Dimethicon/Methicon Copolymer | 3.00 |
| *Butyrospermum parkii* (Shea Butter) | 1.00 |
| $C_{12-15}$ alkyl benzoate | 6.50 |
| Butylene glycol | 5.00 |
| Xanthan gum | 0.30 |
| Disodium EDTA | 0.10 |
| Allantoin | 0.10 |
| Polyacryl amide. $C_{13-14}$ isoparaffin. Laureth-7 | 1.00 |
| Pentylene glycol | 5.00 |
| 4-t Butylcyclohexanol | 1.00 |
| Fragrance composition B | 0.30 |
| Preservatives (Methyl-. Butyl-. Ethyl-. Propylparaben. Phenoxyethanol) | 0.30 |
| Substance of formula (I) | 0.60 |
| Aqua dem. | Ad 100 |

TABLE 39

Sun protection spray (Amounts in % b.w.)

| Ingredients | INCI | Amount |
|---|---|---|
| Water. demineralized | Water (aqua) | 69.50 |
| Glycerol | Glycerol | 4.00 |
| 1.3 butylene glycol | Butylene glycol | 5.00 |
| D-Panthenol | Panthenol | 0.50 |
| Lara Care A-200 | Galactoarabinan | 0.25 |
| Baysilone oil M 10 | Dimethicone | 1.00 |
| Edeta BD | Disodium EDTA | 0.10 |
| Copherol 1250 | Tocopheryl acetate | 0.50 |
| Cetiol OE | Dicaprylyl ether | 3.00 |
| Neo Heliopan ® HMS | Homosalate | 5.00 |
| Neo Heliopan ® AV | Ethylhexyl methoxycinnamate | 6.00 |
| Neo Heliopan ® 357 | Butyl methoxydibenzoylmethane | 1.00 |
| Corapan TQ | Diethylhexylnaphthalate | 2.00 |
| Alpha Bisabolol | Bisabolol | 0.10 |
| Pemulen TR-2 | Acrylates/C10-30 alkyl acrylate crosspolymer | 0.25 |
| NaOH. 10% | Sodium hydroxide | 0.60 |
| Fragrance composition B | Fragrance | 0.20 |
| Phenoxyethanol | Phenoxyethanol | 0.40 |
| Solbrol M | Methylparaben | 0.10 |
| Solbrol P | Propylparaben | 0.10 |
| 4-hydroxy-acetophenone | Hydroxyacetophenone | 0.50 |

TABLE 40

Sunscreen spray O/W. SPE 15-20 (Amounts in % b.w.)

| Ingredients | INCI | Amount |
|---|---|---|
| Dracorin ® GOC | Glyceryl Oleate Citrate. Caprylic/Capric Triglyceride | 2.00 |
| Corapan ® TQ | Diethylhexyl 2.6-Naphthalate | 3.00 |
| Neo Heliopan ® HMS | Homosalate | 7.00 |
| Neo Heliopan ® OS | Ethylhexyl Salicylate | 5.00 |
| Neo Heliopan ® 357 | Butyl Methoxydibenzoylmethane | 3.00 |
| Isoadipate | Diisopropyl Adipate | 6.00 |
| Baysilone ® Oil M10 | Dimethicone | 1.00 |
| Edeta ® BD | Disodium EDTA | 0.10 |
| Vitamin E Acetate | Tocopheryl Acetate | 0.50 |
| Dragosantol ® 100 | Bisabolol | 0.10 |
| Pemulen ® TR-2 | Acrylates/C10-30 Alkyl Acrylate Crosspolymer | 0.25 |
| Water | Water (Aqua) | Ad 100 |
| Glycerol 99.5 P. | Glycerol | 4.00 |
| Butylene Glycol | Butylene Glycol | 5.00 |
| Neo Heliopan ® Hydro (103089). used as 25% aq. solution neutralized with Biotive ® L-Arginine | Phenylbenzimidazole Sulfonic Acid | 8.00 |
| Biotive ® L-Arginine | Arginine | 0.55 |
| Fragrance composition B | Fragrance | 0.40 |
| Sobrol M | Methylparaben | 0.30 |
| 4-hydroxy-acetophenone | Hydroxyacetophenone | 0.60 |

TABLE 41

Sun protection soft cream (W/O). SPF 40 (Amounts in % b.w.)

| Ingredients | INCI | Amount |
|---|---|---|
| Dehymuls PGPH | Polyglyceryl-2 dipolyhydroxystearate | 5.00 |
| Copherol 1250 | Tocopheryl acetate | 0.50 |
| Permulgin 3220 | Ozocerite | 0.50 |
| Zinc stearate | Zinc stearate | 0.50 |
| Tegosoft TN | C12-15 Alkyl benzoate | 10.00 |
| Neo Heliopan ® E1000 | Isoamyl-p-methoxycinnamate | 2.00 |
| Neo Heliopan ® 303 | Octocrylene | 5.00 |
| Neo Heliopan ® MBC | 4-Methylbenzylidene camphor | 3.00 |
| Zinc oxide. neutral | Zinc oxide | 5.00 |
| Water. distilled | Water (aqua) | Add 100 |
| EDETA BD | Disodium EDTA | 0.10 |
| Glycerol | Glycerol | 4.00 |
| Magnesium sulfate | Magnesium sulfate | 0.50 |
| Fragrance composition B | Parfum | 0.30 |
| Symdiol ® 68 | 1.2-Hexanediol. Caprylylglycol | 0.30 |
| Substance of formula (I) | | 0.80 |

TABLE 42

Sun protection milk (W/O) (Amounts in % b.w.)

| Ingredients | INCI | Amount |
|---|---|---|
| Dehymuls PGPH | Polyglyceryl-2 dipolyhydroxystearate | 3.00 |
| Beeswax 8100 | Beeswax | 1.00 |
| Monomuls 90-0-18 | Glyceryl oleate | 1.00 |
| Zinc stearate | Zinc stearate | 1.00 |
| Cetiol SN | Cetearyl isononanoate | 5.00 |
| Cetiol OE | Dicaprylyl ether | 5.00 |
| Tegosoft TN | C12-15 alkyl benzoate | 4.00 |
| Vitamin E | Tocopherol | 0.50 |
| Neo Heliopan ® OS | Ethylhexyl salicylate | 5.00 |
| Neo Heliopan ® AV | Ethylhexyl methoxycinnamate | 7.50 |
| Uvinul ® T150 | Ethylhexyl triazone | 1.50 |
| Water. distilled | Water (Aqua) | To 100 |
| Trilon BD | Disodium EDTA | 0.10 |
| Glycerol | Glycerol | 5.00 |

TABLE 42-continued

Sun protection milk (W/O) (Amounts in % b.w.)

| Ingredients | INCI | Amount |
|---|---|---|
| Neo Heliopan ® AP 10% solution. neutralized with NaOH | Disodium phenyl dibenzimidazole tetrasulfonate | 15.00 |
| Fragrance composition B | Parfum | 0.25 |
| Alpha bisabolol | Bisabolol | 0.10 |
| SymOcide ® PT | Phenoxyethanol. Tropolone | 0.25 |
| 4-hydroxyacetophenone | Hydroxyacetophenone | 0.25 |

TABLE 43

After sun gel (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 3.000 |
| Glycerol 99.5 P. | Glycerol | 5.000 |
| SymHelios ® 1031 | Benzylidene Dimethoxydimethylin danone | 0.100 |
| Water | Water (Aqua) | Ad 100 |
| Pemulen ® TR-2 | Acrylates/C10-30 Alkyl Acrylate Crosspolymer | 1.000 |
| D-Panthenol 75 W | Panthenol | 0.500 |
| SymFinity ® 1298 | *Echinacea Purpurea* Extract | 0.100 |
| Extrapone ® Pearl GW | Water (Aqua). Glycerol. Hydrolyzed Pearl. Xanthan Gum | 1.000 |
| Sodium Hydroxide 10% solution | Sodium Hydroxide | 2.500 |
| Ethanol 96% | Alcohol Denat. | 15.000 |
| Fragrance composition B | Parfum | 0.20 |
| SymOcide ® PS | Phenoxyethanol. 1.2-Hexanediol. Decyleneglycol | 0.50 |
| 4-hydroxy-acetophenone | Hydroxyacetophenone | 0.50 |

TABLE 44

After sun lotion (Amounts in % b.w.)

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Fragrance composition B | 0.30 |
| 1.2-Hexanediol | 0.60 |
| Hydroxyacetone | 0.30 |
| Pentylene glycol | 4.0 |
| Aqua dem. | Ad 100 |
| Triethanolamine | 0.2 |

TABLE 45

Hair styling gel (Amounts in % b.w.)

| Ingredients | Amount |
|---|---|
| Water | Ad 100 |
| PVM/MA Decadiene Crosspolymer | 0.60 |
| PVP | 3.00 |
| Isocetyl Stearate | 4.00 |
| Ethylhexyl Methoxycinnamate | 0.50 |

TABLE 45-continued

Hair styling gel (Amounts in % b.w.)

| Ingredients | Amount |
|---|---|
| Aminomethyl Propanol | 0.40 |
| Fragrance composition B | 0.60 |
| SymDiol ® 68T (1.2-Hexanediol. 1.2-Octanediol. Tropolone) | 0.30 |
| Phenoxyethanol | 0.20 |
| Hydroxyacetophenone | 0.40 |

TABLE 46

Silicone emulsion (Amounts in % b.w.)

| Ingredients | Amount |
|---|---|
| Potassium Cetyl Phosphate. Hydrogenated Palm Glycerides | 1.00 |
| Cyclohexasiloxane | 4.00 |
| Cetearyl Alcohol | 1.50 |
| Phenyl Trimethicone | 3.00 |
| Stearyl Heptanoate. Stearyl Caprylate | 3.00 |
| Dimethicone | 1.00 |
| Xanthan Gum | 0.20 |
| Isoamyl p-Methoxycinnamate | 5.00 |
| Water | Ad 100 |
| Methylpropanediol | 3.00 |
| Fragrance composition B | 0.30 |
| Diazolidinyl urea | 0.10 |

TABLE 47

Microemulsion gel (Amounts in % b.w.)

| Ingredient | Amount |
|---|---|
| Glycerol isostearate | 1.80 |
| Octoxyglycerol | 1.00 |
| Ceteareth-15 | 5.20 |
| PEG-150 Distearate | 1.00 |
| Aluminium chlorohydrate | 5.00 |
| Isotridecylisononanoate | 3.30 |
| Cyclomethicone | 6.60 |
| Fragrance composition B | 0.70 |
| Euxyl ® K145 (Methylchloroisothiazolinone. Methylisothiazlinone. Bronopol) | 0.10 |
| Hydroxyacetophenone | 0.40 |
| Water | Ad 100 |

TABLE 48

Air freshener in gel form (Amounts in % b.w.)

| Ingredient | Amount |
|---|---|
| Demineralised water | Ad 100 |
| Genugel ® X-6424 (carrageenan) | 2.00 |
| Arkopal ® N 100 or Tergitol ® NP 10 (Emulsifer) | 3.50 |
| Fragrance composition B | 0.60 |
| Preventol ® D 7 (5-chloro-2-methyl-4-isothiazolin-3-one. 2-methyl-2H isothiazol-3-one) | 0.10 |
| Substance of formula (I) | 0.80 |

TABLE 49

Cleaner. APC liquid. alkaline pH 8-10 (Amounts in % b.w.)

| Ingredients (INCI) | Amount |
|---|---|
| Aqua | 59.06 |
| Tri Sodium Citrate Dihydrate | 3.00 |
| Sodium Laureth Sulfate | 30.00 |

TABLE 49-continued

Cleaner. APC liquid. alkaline pH 8-10 (Amounts in % b.w.)

| Ingredients (INCI) | Amount |
| --- | --- |
| Trideceth-9 | 5.00 |
| Ethanol | 2.00 |
| Citric Acid 10% solution | 0.24 |
| Fragrance composition B | 0.50 |
| Mixture of 5-Chloro-2-methyl-2H-isothiazol-3-one and 2-Methyl-2H-isothiazol-3-one | 0.10 |
| Hydroxyacetophenone | 0.30 |

TABLE 50

Fabric softener (Amounts in % b.w.)

| Ingredients (INCI) | Amount |
| --- | --- |
| Aqua | 72.10 |
| Dialkylester ammomium methosulfate | 16.60 |
| Polydimethylsiloxane | 0.30 |
| Magnesiumchloride | 10.00 |
| Perfume oil P1. P2. P3 or P4 | 0.60 |
| Mixture of 5-Chloro-2-methyl-2H-isothiazol-3-one and 2-Methyl-2H-isothiazol-3-one | 0.10 |
| Hydroxyacetophenone | 0.40 |

TABLE 51

Liquid detergent (Amounts in % b.w.)

| Ingredients | Amount |
| --- | --- |
| Deionized water | 39.60 |
| Optical brightener | 0.10 |
| Coconut fatty acids (C12-C18) | 7.50 |
| Potassium hydroxide 50% solution | 4.30 |
| Propane-1.2-diol | 5.00 |
| Fatty alcohols C12-C15. 8 EO | 12.00 |
| Na-salt of secondary alkyl sulfonates (C13-C17) | 17.00 |
| Triethanolamine | 2.00 |
| Trisodium citrate dihydrate | 5.00 |
| Dequest 2066 Diethylenetriamine penta(methylene phosphonic acid) | 3.00 |
| Ethanol | 3.00 |

TABLE 51-continued

Liquid detergent (Amounts in % b.w.)

| Ingredients | Amount |
| --- | --- |
| Enzymes | 0.70 |
| Fragrance composition B | 0.50 |

TABLE 52

Liquid detergent concentrate (Amounts in % b.w.)

| Ingredients | Amount |
| --- | --- |
| Deionized water | 12.9 |
| Coconut fatty acids (C12-C18) | 10.0 |
| Fatty alcohols C12-C15. 8 EO | 26.0 |
| Na-salt of secondary alkyl sulfonates (C13-C17) | 26.5 |
| Triethanol amine | 8.5 |
| Na-salt of fatty alcohol sulfates C12-C14 | 3.0 |
| Ethanol | 5.5 |
| Urea | 4.5 |
| Enzymes | 0.9 |
| Citric acid | 1.0 |
| Fragrance composition B | 0.7 |
| Hydroxyacetophenone | 0.8 |

TABLE 53

Solution for wet wipes (Amounts in % b.w.)

| Ingredients | INCI | Amount |
| --- | --- | --- |
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 2.00 |
| Dragosantol ® 100 | Bisabolol | 0.10 |
| Glycerol 99.5 P. | Glycerol | 5.00 |
| Water | Water (Aqua) | Ad 100 |
| Hydrolite ® 5 | Pentylene Glycol | 5.00 |
| D-Panthenol 75 W | Panthenol | 0.80 |
| DragoCalm ® | Water (Aqua). Glycerol. *Avena Sativa* (Oat) Kernel Extract | 1.00 |
| Witch Hazel-Distillate | *Hamamelis Virginiana* (Witch Hazel) Water. Water (Aqua). Alcohol | 1.00 |
| Allplant Essence ® Org. Rose Geranium P | *Pelargonium Graveolens* Flower/Leaf/Stem Water | 1.00 |
| Fragrance composition B | Parfum | 0.10 |
| Preservative | Phenoxyethanol | 0.30 |
| 4-hydroxyacetophenone | Hydroxyacetophenone | 0.50 |

TABLE 54

Toothpaste (Amounts in % b.w.)

| Ingredients | Amount |
| --- | --- |
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sodiumcarboxymethylcellulose | 1.10 |
| Titanium (IV) oxide | 0.50 |
| Water (deionized) | 4.50 |
| Sodiumlaurylsulfate (SLS) | 1.50 |

TABLE 54-continued

Toothpaste (Amounts in % b.w.)

| Ingredients | Amount |
| --- | --- |
| Fragrance composition B | 1.00 |
| Solbrol M (Sodium salt) (Methylparaben) | 0.15 |
| Hydroxyacetophenone | 0.40 |

TABLE 55

Toothpaste with zinc citrate (Amounts in % b.w.)

| Ingredients | Amount |
| --- | --- |
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sodiumcarboxymethylcellulose | 1.10 |
| Zinc citrate | 1.00 |
| Titanium (IV) oxide | 0.50 |
| Water (deionized) | 4.50 |
| Sodiumlaurylsulfate (SLS) | 1.50 |
| Fragrance composition B | 1.00 |
| SymDiol ® 68 (1.2-Hexanediol. Caprylylglycol) | 0.25 |
| Hydroxyacetophenone | 0.10 |

TABLE 56

Mouth rinse (Amounts in % b.w.)

| Ingredients | Amount |
| --- | --- |
| Ethylalcohol | 10.00 |
| Cremophor CO 40 (PEG 40 hydrogenated castor oil) | 1.00 |
| Fragrance composition B | 0.25 |
| Water (deionized) | To 100.00 |
| Sorbitol 70% | 5.00 |
| Sodiumsaccharin 450 | 0.07 |
| Sodiumfluoride | 0.18 |
| Benzoic acid | 0.12 |
| Hydroxyacetophenone | 0.30 |

TABLE 57

Gel dental cream (Amounts in % b.w.)

| Ingredients | Amount |
| --- | --- |
| Na carboxymethylcellulose | 0.40 |
| Sorbitol 70%. in water | 72.00 |
| Polyethylene glycol (PEG) 1500 | 3.00 |
| Na saccarinate | 0.07 |
| Na fluoride | 0.24 |
| Fragrance composition B | 1.00 |
| Abrasive silica | 11.00 |
| Thickening silica | 6.00 |
| Sodium dodecyl sulfate (SDS) | 1.40 |
| Dist. water | Ad 100 |
| p-Hydroxybenzoic acid (PHB) ethyl ester | 0.15 |
| 4-hydroxyacetophenone | 0.20 |

TABLE 58

Dental cream against plaque (Amounts in % b.w.)

| Ingredients | Amount |
| --- | --- |
| Carrageenan | 0.90 |
| Glycerol | 15.00 |
| Sorbitol 70%. in water | 25.00 |
| PEG 1000 | 3.00 |
| Na fluoride | 0.24 |
| Tetrapotassium diphosphate | 4.50 |
| Tetrasodium diphosphate | 1.50 |
| Na saccarinate | 0.40 |
| Precipitated silica | 20.00 |
| Titanium dioxide | 1.00 |
| Triclosan | 0.30 |
| Spearmint flavor (comprising 60 wt. % l-carvone and 25 wt. % l-menthol) | 1.00 |
| Sodium dodecyl sulfate | 1.30 |
| Dist. water | Ad 100 |
| Benzylalcohol | 0.50 |
| Fragrance composition B | 0.25 |

TABLE 59

Dental cream for sensitive teeth (Amounts in % b.w.)

| Ingredients | Amount |
| --- | --- |
| Na carboxymethylcellulose | 0.70 |
| Xanthan gum | 0.50 |
| Glycerol | 15.00 |
| Sorbitol 70%. in water | 12.00 |
| Potassium nitrate | 5.00 |
| Sodium monofluorophosphate | 0.80 |
| Fragrance composition B | 1.00 |
| Ca-carbonate | 35.00 |
| Silicon dioxide | 1.00 |
| Sodium dodecyl sulfate (SDS) | 1.50 |
| Dist. water | Ad 100 |
| PHB methyl ester and PHB propyl ester | 0.20 |

TABLE 60

Tooth cream and mouthwash 2-in-1 product (Amounts in % b.w.)

| Ingredients | Amount |
| --- | --- |
| Sorbitol | 40.00 |
| Glycerol | 20.00 |
| Ethanol | 5.00 |
| Water | Ad 100 |
| Na monofluorophosphate | 0.75 |
| Saccharin | 0.20 |
| Sident 9 (abrasive silicon dioxide) | 20.00 |
| Sident 22 S (thickening silicon dioxide) | 2.00 |
| Sodium carboxymethylcellulose | 0.30 |
| Sodium lauryl sulfate (SDS) | 1.20 |
| Color (Suspension. 1% in water) C.I. Pigment Blue 15 | 0.50 |
| Fragrance composition B | 0.90 |
| Solbrol M. sodium salt (methylparaben. sodium salt) | 0.20 |

TABLE 61

Ready-to-use mouthwash with fluoride (Amounts in % b.w.)

| Ingredients | Amount |
| --- | --- |
| Ethanol | 7.00 |
| Glycerol | 12.00 |
| Na fluoride | 0.05 |
| Pluronic F-127 ® (BASF. surface-active substance) | 1.40 |
| Na phosphate buffer pH 7.0 | 1.10 |
| Na saccharinate | 0.10 |

TABLE 61-continued

Ready-to-use mouthwash with fluoride (Amounts in % b.w.)

| Ingredients | Amount |
| --- | --- |
| Fragrance composition B | 0.15 |
| Chlorhexidine digluconate | 0.2 |
| Dist. water | to 100 |
| Sorbic acid | 0.20 |

TABLE 62

Sugar-free chewing-gum (Amounts in % b.w.)

| Ingredients | Amount |
| --- | --- |
| Chewing gum base | 30.00 |
| Sorbitol. powder | Ad 100 |
| Palatinite | 9.50 |
| Xylitol | 2.00 |
| Mannitol | 3.00 |
| Aspartame | 0.10 |
| Acesulfame K | 0.10 |
| Emulgum/emulsifier | 0.30 |
| Sorbitol 70%. in water | 14.00 |
| Glycerol | 1.00 |
| Fragrance composition B | 1.50 |
| Substance of formula (I) | 0.20 |

TABLE 63

Bar soaps

| Ingredients | A1 | A2 | A3 |
| --- | --- | --- | --- |
| Sodium C12/14 Olefin Sulphonate | 40.0 | — | — |
| Disodium Lauryl Sulphosuccinate | — | 40.0 | — |
| Lauryl Glucoside | 15.0 | 15.0 | 55.0 |
| Cetylstearyl Alcohol | 12.0 | 12.0 | 12.0 |
| Paraffin Oil (m.p. 54 to 56° C.) | 8.0 | 8.0 | 8.0 |
| Maize Starch, degraded | 8.0 | 8.0 | 8.0 |
| Palmitic Acid (and) Stearic Acid | 5.5 | 5.5 | 5.5 |
| Glyceryl Stearate | 2.0 | 2.0 | 2.0 |
| Coco Glyceride | 2.0 | 2.0 | 2.0 |
| Polyquaternium-7 | 1.0 | 1.0 | 1.0 |
| Perfume oil | 1.0 | 1.0 | 1.0 |
| Titanium dioxide | 0.5 | 0.5 | 0.5 |
| Fragrance composition B | 0.05 | 0.05 | 0.05 |
| Water | | ad 100 | |

TABLE 64

Syndet soaps

| Ingredients | B1 | B2 | B3 |
| --- | --- | --- | --- |
| Lauryl Glucoside | 15.0 | 15.0 | 15.0 |
| Sodium C12/14 Olefin Sulphonate | 40.0 | 40.0 | — |
| Sodium Lauryl Sulphate | — | — | 40.0 |
| Paraffin Oil (m.p. 54° C.) | 8.0 | 8.0 | 8.0 |
| Tallow Fatty Alcohol | 7.0 | 7.0 | 7.0 |
| Maize starch | 17.0 | — | 17.0 |
| Dextrose | — | 17.0 | — |
| Coco Fatty Acids | 10.0 | 10.0 | 10.0 |
| Titanium dioxide | 1.0 | 1.0 | 1.0 |
| Perfume oil | 1.0 | 1.0 | 1.0 |
| Fragrance composition B | 0.05 | 0.05 | 0.05 |
| Water | | ad 100 | |

TABLE 65

WC gel toilet blocks

| Ingredients | C1 | C2 | C3 | C4 | C5 | C6 |
| --- | --- | --- | --- | --- | --- | --- |
| Lauryl Glucoside | 5.0 | 1.5 | 1.5 | 1.5 | 5.0 | 1.5 |
| Decyl Glucoside | — | 3.5 | 3.5 | 3.5 | — | 3.5 |
| Sodium Lauryl Sulphate | 9.0 | 6.0 | 3.0 | — | 9.0 | 6.0 |
| Sodium Laureth Sulphate | — | 3.0 | — | — | — | 3.0 |
| Cocamidopropyl Betaine | — | — | 6.0 | 9.0 | — | — |
| Ethanol | 3.5 | 3.5 | 3.5 | 3.5 | 3.5 | 3.5 |
| Citric Acid Mono Hydrate | 3.6 | 3.6 | 3.6 | 3.6 | 3.6 | 3.6 |
| Sodium Hydroxide | 0.5 | 0.5 | 0.5 | 0.5 | 0.5 | 0.5 |
| Laurylamine + 1EO | 4.5 | 3.0 | 5.0 | 2.5 | — | — |
| Hexanediol-1,6 | — | 0.5 | — | — | 0.5 | — |
| Perfume oil | 0.5 | 0.5 | 0.5 | 0.5 | 0.5 | 0.5 |
| Fragrance composition C | 0.05 | 0.05 | 0.05 | 0.05 | 0.05 | 0.05 |
| Water | | | ad 100 | | | |

TABLE 66

Powder detergents

| Ingredients | E1 | E2 | E3 | E4 | E5 | E6 |
| --- | --- | --- | --- | --- | --- | --- |
| Sodium Laureth-1 Sulphate | 12.0 | 8.0 | 8.0 | 4.0 | 4.0 | — |
| Dodecylbenzene sulphonate | — | — | 4.0 | 8.0 | 4.0 | 8.0 |
| Sodium Lauryl Sulphate | — | 4.0 | — | — | 4.0 | 4.0 |
| Coco Fatty Acid, Sodium Salt | 1.0 | 1.0 | 1.0 | 1.0 | 1.0 | 1.0 |
| Coco Glucosides | — | — | — | 7.0 | — | — |
| Laureth-5 | 7.0 | 7.0 | 7.0 | — | 7.0 | 7.0 |
| Zeolite A | 24.0 | 24.0 | 24.0 | 24.0 | 24.0 | 24.0 |
| Sodium silicate, amorphous (modulus 1:2) | 3.0 | 3.0 | 3.0 | 3.0 | 3.0 | 3.0 |
| Sodium carbonate | 12.0 | 12.0 | 12.0 | 12.0 | 12.0 | 12.0 |
| Polymeric polycarboxylate | 5.5 | 5.5 | 5.5 | 5.5 | 5.5 | 5.5 |
| Perborate monohydrate | 16.0 | 16.0 | 16.0 | 16.0 | 16.0 | 16.0 |
| Tetraacetylethylenediamine | 5.5 | 5.5 | 5.5 | 5.5 | 5.5 | 5.5 |
| Carboxymethylcellulose | 0.3 | 0.3 | 0.3 | 0.3 | 0.3 | 0.3 |
| Optical brightener | 0.2 | 0.2 | 0.2 | 0.2 | 0.2 | 0.2 |
| Enzyme granules (protease) | 1.0 | 1.0 | 1.0 | 1.0 | 1.0 | 1.0 |
| Perfume oil | 0.5 | 0.5 | 0.5 | 0.5 | 0.5 | 0.5 |
| Fragrance composition C | 0.05 | 0.05 | 0.05 | 0.05 | 0.05 | 0.05 |
| Water | | | ad 100 | | | |

The invention claimed is:

1. A fragrance mixture consisting of (a) at least one compound of general formula (I)

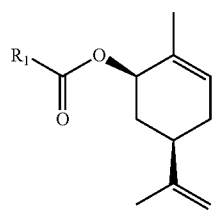

in which R1 stands for methyl, ethyl, methoxy or ethoxy;

(b) at least one compound of general formula (II)

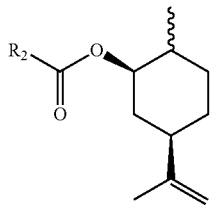

in which R2 stands for methyl, ethyl, methoxy or ethoxy;

(c) at least one additional fragrance, different from compounds (I) and (II) which is selected from the group consisting of melonal, triplal, ligustral, adoxal, anisaldehyde, cymal, ethylvanillin, florhydral, floralozon, helional, heliotropin, hydroxycitronellal, koavon, laurinaldehyde, canthoxal, lyral, lilial, adoxal, anisaldehyde, cumal, methyl-nonyl-acetaldehyde, citronellal, citronellyloxy-acetaldehyde, cyclamenaldehyde, bourgeonal, p-tert.-bucinal, phenylacetaldehyde, undecylenaldehyde, vanillin; 2,6,10-trimethyl-9-undecenal, 3-dodecen-I-al, α-n-Amylzimtaldehyde, 4-methoxybenz-aldehyde, benzaldehyde, 3-(4-tert-butylphenyl)-propanal,2-methyl-3-(para-methoxy-phe-nylpropanal), 2-methyl-4-(2,6,6-trimethyl-2(1)-cyclohexen-1-yl)butanal,3-phenyl-2-pro-penal, cis-/trans-3,7-dimethyl-2,6-octadien-I-al, 3,7-dimethyl-6-octen-I-al, [(3,7-dimethyl-6-octenyl)-xy]-cetaldehyde, 4-isopropylbenzaldehyde, 1,2,3,4,5,6,7,8-octahydro-8,8-dimethyl-2-naphthaldehyde, 2,4-dimethyl-3-cyclohexen-1-carboxyaldehyde, 2-methyl-3-(isopropyl-phenyl)propanal, decyl aldehyde, 2,6-dimethyl-5-heptenal; 4-(tricyclo [5.2.1.0 (2,6)] -decylidene-8)-butanal; octahydro-4,7-methano-IH-indenecarboxaldehyde; 3-ethoxy-4-hydroxybenzaldehyde, para-ethyl-alpha,alpha-dimethylhydrozimtaldehyde, α-methyl-3,4-(methylenedioxy)-hydrocinnamaldehyde, 3,4-methylenedioxybenzaldehyde, α-n-hexyl-cinnamaldehyde, m-cymene-7-carboxaldehyde, a-methylphenylacetaldehyde, 7-hydroxy-3,7-dimethyl octanal, undecenal, 2,4,6-trimethyl-3-cyclohexene-I-carboxalde-hyde, 4-(3)(4-methyl-3-pentenyl)-3-cyclohexen-carboxaldehyde, 1-dodecanal, 2,4-dimethyl-cyclohexene-3-carboxaldehyde, 4-(4-hydroxy-4-methylpentyl)-3 -cylohexene-I-carboxal-dehyde, 7-methoxy-3,7-dimethyloctan- 1-al, 2-methyl undecanal, 2-methyl decanal, 1-nonanal, 1-octanal, 2,6,10-trimethyl-5,9-undecadienal, 2-methyl-3 -(4-tertbutyl)propanal, 3-(4-ethylphenyl)-2,2-dimethylpropanal, 3-(4-methoxyphenyl)-2-methylpropanal, methylno-nylacetaldehyde, 2-phenylpropan- 1-al, 3-phenylprop-2-en-1-al, 3-phenyl-2-pentylprop-2-en-1-al, 3-phenyl-2-hexylprop-2-en-1al, 3-(4-isopropylphenyl)-2-methylpropan-1-al, 3-(4-ethylphenyl)-2,2-dimethylpropan-1-al, 3-(4-tert-butylphenyl)-2-methyl-propanal, 3-(3,4-Methylendioxy-phenyl) -2-methylpropan-1-al3-(4-Ethylphenyl)-2,2-dimethylpropanal, 3-(3-Isopropylphenyl)-butan-1-al, 2,6-Dimethylhept-5-en-1-al, Dihydrozimtaldehyde, 1-methyl-4-(4-methyl-3-pentenyl)-3-cyclohexene-1-carboxaldehyde, 5- or 6-Methoxyhexahydro-4,7-methanoindan-1 or 2-carboxyaldehyde, 3,7-dimethyl-octan-l-al, 1-undecanal, 10-undecen-1-al, 4-hydroxy-3 -methoxybenzaldehyde, 1-methyl-3-(4-methylpentyl)-3-cyclohexene-carboxy aldehyde, 7-hydroxy-3,7-dimethyl-octanal; trans-4-decenal, 2,6-nonadienal, p-tolylacetaldehyde; 4-methylphenylacetaldehyde, 2-methyl-4-(2,6,6-trimethyl-1-cyclohexen-l-yl)-2-butenal, o-methoxyzimtaldehyde, 3,5,6-trimethyl-3-cyclohexenecarboxaldehyde, 3,7-dimethyl-2-methylene-6-octenal, phenoxyacetaldehyde; 5,9-dimethyl-4,8-decadienal, peony aldehyde (6,10-dimethyl-3 -oxa-5,9-undecadien-1-al), hexahydro-4,7-methanoindan-1-carboxaldehyde, octanal, 2-methyl octanal, alpha-methyl-4-(I-methylethyl)benzene-acetaldehyde, 6,6-dimethyl-2-norpinene-2-propionaldehyde, p-methyl phenoxy acetaldehyde, 2-methyl-3-phenyl-2-propen-1-al, 3,5,5-trimethylhexanal, hexahydro-8,8-dimethyl-2-naphthaldehyde, 3-propyl-bicyclo[2.2.1]-hept-5 -ene-2-carbaldehyde, 9-decenal, 3-methyl-5-phenyl-1-pentanal, methylnonyl acetaldehyde, 1-p-menthene-q-carboxaldehyde, citral or its mixtures, lilial citral, 1-decanal, n-undecanal, n-dodecanal, hlorhydral, 2,4-dimethyl-3-cyclohexen-1-carboxaldehyde 4-methoxybenzaldehyde, 3-methoxy-4-hydroxy-benzalde-hyde, 3-ethoxy-4-hydroxybenzaldehyde, 3,4-methylendioxybenzaldehyde, 3,4-dimethoxybenzaldehydebuccoxime, iso jasmone, methyl beta naphthyl ketone, moschus indanone, tonalid/moschus plus, α-damascone, β-damascon, δ-damascone, Iso-damascone, damascenone, damarose, methyl-dihydrojasmonate, fenchone, alphalonen, y-methylionone, fleuramone, dihydrojasmone, cis-Jasmon, iso-E-Super, methyl cedrenylk etone, or methyl cedrylon, acetophenone, methyl aceto phenone, p-methoxyacetophenone, methyl-β-naphtyl ketone, benzylacetone, benzophenone, p-hydroxy phenylbutanone, celery Ketone or livescon, 6-osopropyl-deca-hydro-2-naphtone, dimethyloctenone, freskomenth, 4-(I-ethoxyvinyl)-3,3,5,5,-tetramethylv cyclohexanone, methylheptenone, 2-(2-(4-Methyl-3-cyclohexen-1-yl) propyl)-cyclopentanone, 1-(p-men-thene-6(2)-yl)-1-propanone, 4-(4-Hydroxy-3-methoxyphenyl)-2-butanone, 2-Acetyl-3,3-dimethyl-norbornan, 6,7-dihydro-1,1,2,3,3-pentamethyl-4(5H)-indanone, 4-damascol, dulcinyl or cassione, gelsone, hexalone, isocyclemone E, Methylcyclocitrone, methyl lavender ketone, orivone, p-tert-butyl cyclohexanone, verdone, delphone, muscone, neobutenone, plicatone, veloutone, 2,4,4,7-tetramethyl-oct-6-en-3-one, tetrameran, hedion, δ-damascone, benzylacetone, damascenone, methyl dihydrojasmonate, methyl cedrylone, hedione, 10-undecen-1-ol, 2,6-dimethylheptan-2-ol, 2-methylbutanol, 2-methylpentanol, 2-phenoxyethanol, 2-phenylpropanol, 2-tert-Butycyclohexanol, 3,5,5-trimethylcyclohexanol, 3-hexanol, 3-methyl-5-phenylpentanol, 3-phenylpropanol,4-heptenol, 4-isopropylcyclohexanol, 4-tert-butycyclohexanol, 6,8-dimethyl-2-nonanol, 6-nonen-1-ol, 9-decen-1-ol, α-methyl benzylalcohol, α-terpineol, amylsalicylat, benzyl alcohol, benzyl salicylate, β-terpineol, butyl salicylate, citronellol, cyclohexyl salicylate, decanol, dihydromyrcenol, dimethyl benzylcarbinol, dimethyl heptanol, dimethyl octanol, ethyl salicylate, ethyl vanilin, eugenol, geraniol, heptanol, hexyl salicylat, isoborneol, isoeugenol, isopulegol, menthol, myrtenol, n-hexanol, nerol, nonanol, paramenthan-7-ol, phenylethylalkohol, phenol, phenyl salicylat, tetrahydro geraniol, tetrahydro linalool, thymol, trans-2-cis-6-nonadienol, trans-2-nonen-1-ol, trans-2-octenol, undecanol, vanillin, cinnamalcohol, encompass benzyl acetate, phenoxyisobutyrate, p-tert.-butylcyclohexylacetate, linalylacetate, dimethylbenzylcarbinylacetate (DMBCA), phenylethylacetate, benzylacetate, ethylmethylphenylglycinate, allylcyclohexylpropionate, styrallylpropionate, benzylsalicylate, cyclohexylsalicylate, floramat, melusat, jasmacyclatat, benzylethyl ether, ambroxan; and, (d) at least one solvent selected from the group consisting of ethanol, isopropyl alcohol, ethylene glycol, diethylene glycol, diethylene glycol monomethyl ether, diethylene glycol monoethyl ether, propylene glycol, dipropylene glycol, 1,2-butylene glycol, glycerol, diethyl phthalate, triethyl citrate, isopropyl myristate and its mixtures,
wherein
(i) components (a+b) and (c+d) both have an unpleasant fragrance, which is not present when components (a+b) are added to components (c+d); and,
(ii) components (a+b) are present in the mixture (a+b+c+d) in amounts of from 0.001 to 0.1 wt. percent—calculated on the mixture.

2. The mixture of claim 1, consisting of as component (b) a compound of general formula (IIa)

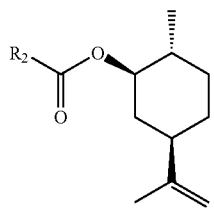

in which R2 stands for methyl, ethyl, methoxy or ethoxy.

3. The mixture of claim 2 further consisting of at least one compound of formula (III)

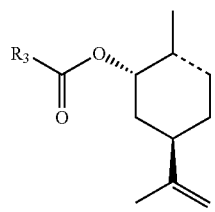

in which R3 stands for methyl, ethyl, methoxy or ethoxy and the dotted line means a single or double bond.

4. The mixture of claim 3 consisting of
(i) about 62 to about 67% b.w. of at least one 1R,5R isomer of compound (I);
(ii) about 14 to about 18% b.w. of at least one 1R,2R,5R isomer of compound (IIa);
(iii) about 6.0 to about 7.0% b.w. of at least one 1S,2R,5S isomer of compound (II);
(iv) about 7.0 to about 9.0% b.w. of at least one 1R,5S isomer of compound (III);
(v) about 4.0 to about 6.0% b.w. of at least one 1R,2S,5S isomer of formula (III); and
(vi) about 0.5 to about 1.0% b.w. of at least one 1R,2R,5S isomer of formula (III) on condition that the amounts add to 100% b.w.

5. The mixture of claim 1, wherein said fragrance has a molecular mass of about 100 to about 250 Dalton.

6. The mixture of claim 1 consisting of components (a) and (b) in a ratio by weight of from about 1:99 to about 99:1.

7. A perfume composition comprising the fragrance mixture of claim 1.

8. The composition of claim 7, comprising about 0.001 to about 75% b.w. of the fragrance mixture.

9. A cosmetic or household composition comprising the mixture of claim 1.

10. A method for improving the olfactory aspects and/or for preventing unpleasant olfactory aspects of a fragrance, comprising the step of providing a fragrance in need of olfactory support and applying the mixture of claim 1.

* * * * *